US008637053B2

(12) United States Patent
Higgins et al.

(10) Patent No.: US 8,637,053 B2
(45) Date of Patent: Jan. 28, 2014

(54) *CHLAMYDIA* ANTIGENS

(75) Inventors: Darren E. Higgins, Jamaica Plain, MA (US); Todd Gierahn, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 12/746,155

(22) PCT Filed: Dec. 3, 2008

(86) PCT No.: PCT/US2008/013298
§ 371 (c)(1),
(2), (4) Date: Jun. 24, 2010

(87) PCT Pub. No.: WO2009/073179
PCT Pub. Date: Jun. 11, 2009

(65) Prior Publication Data
US 2010/0278854 A1    Nov. 4, 2010

Related U.S. Application Data

(60) Provisional application No. 61/005,209, filed on Dec. 3, 2007.

(51) Int. Cl.
*A61K 39/118* (2006.01)
*C07K 14/195* (2006.01)

(52) U.S. Cl.
USPC ............... 424/263.1; 424/185.1; 424/190.1; 424/192.1; 530/350

(58) Field of Classification Search
None
See application file for complete search history.

(56) References Cited

U.S. PATENT DOCUMENTS

| | | | |
|---|---|---|---|
| 6,008,415 A | 12/1999 | Greene et al. | |
| 6,248,329 B1 * | 6/2001 | Chandrashekar et al. . | 424/191.1 |
| 6,565,856 B1 | 5/2003 | Skeiky et al. | |
| 7,041,490 B1 * | 5/2006 | Griffais et al. ............. | 435/252.3 |
| 2002/0061848 A1 | 5/2002 | Bhatia et al. | |
| 2002/0146776 A1 | 10/2002 | Bhatia et al. | |
| 2003/0175700 A1 | 9/2003 | Bhatia et al. | |
| 2004/0137007 A1 | 7/2004 | Bhatia et al. | |
| 2004/0234536 A1 | 11/2004 | Bhatia et al. | |
| 2005/0084499 A1 | 4/2005 | Bhatia et al. | |
| 2005/0152926 A1 | 7/2005 | Bensi et al. | |
| 2005/0232941 A1 | 10/2005 | Bhatia et al. | |

FOREIGN PATENT DOCUMENTS

| | | |
|---|---|---|
| WO | WO-99/27105 A2 | 6/1999 |
| WO | WO 99/28475 | 6/1999 |
| WO | WO9928475 A2 * | 6/1999 |
| WO | WO 00/37494 | 6/2000 |
| WO | WO 2007/110700 | 10/2007 |

OTHER PUBLICATIONS

Witkowski et al , Biochemistry 38:11643-11650, 1999.*
Houghten et al (Vaccines, 1986, Edited by Fred Brown: Cold Spring Harbor Laboratory).*
Feng et al (Infection and Immunity, 64(1):363-365, 1996).*
Ellis, R.W. (Chapter 29 of "Vaccines" [Plotkin, S.A. et al. (eds) published by W. B. Saunders company (Philadelphia) in 1988.*
The Dictionary of Immunology, Herbert et al eds, Academic Press, 1995,definition of vaccine, three pages.*
Accession No. H71560 (sequence version available Sep. 13, 1998).*
International Search Report from PCT/US08/13298, completed Apr. 21, 2009, mailed May 4, 2009.
Written Opinion of the International Searching Authority from PCT/US08/13298, completed Apr. 21, 2009, mailed May 4, 2009.
Chen et al., "Genetic fusion of proteins to the SIV Tat protein enhances their immunogenicity," *Vaccine* 24: 708-715 (2006).
Cotter et al., "Protective efficacy of major outer membrane protein-specific immunoglobulin A (IgA) monoclonal antibodies in a murine model of *Chlamydia trachomatis* genital tract infection," *Infect. Immun.* 63: 4704-4714 (1995).
Fan et al., "Immunological properties of recombinant *Mycobacterium bovis* bacillus Calmette-Guérin strain expressing fusion protein IL-2-ESAT-6," *Acta. Biochim. Biophys. Sin.* 38: 683-690 (2006).
Hassell et al., "Identification of T-cell stimulatory antigens of *Chlamydia trachomatis* using synovial fluid-derived T-cell clones," *J. Immunol.* 79: 513-519 (1993).
Huleatt et al., "Vaccination with recombinant fusion proteins incorporating Toll-like receptor ligands induces rapid cellular and humoral immunity," *Vaccine* 8: 763-775 (2007).
Lee et al., "The prolonged half-lives of new erythropoietin derivatives via peptide addition," *Biochem. Biophys. Res. Commun.* 339: 380-385 (2006).
Lois et al., "Germline transmission and tissue-specific expression of transgenes delivered by lentiviral vectors," *Science* 295: 868-872 (2002).
Murby et al., "Hydrophobicity engineering to increase solubility and stability of a recombinant protein from respiratory syncytial virus," *Eur. J. Biochem.* 230: 38-44 (1995).
Pal et al., "Vaccination of mice with DNA plasmids coding for the *Chlamydia trachomatis* major outer membrane protein elicits an immune response but fails to protect against a genital challenge," *Vaccine* 17: 459-465 (1999).
Pal et al., "Immunization with an acellular vaccine consisting of the outer membrane complex of *Chlamydia trachomatis* induces protection against a genital challenge," *Infect Immun.* 65: 3361-3369 (1997).
Schulze et al., "The FAI protein of group C streptococci targets B-cells and exhibits adjuvant activity," *Vaccine* 23: 1408-1413 (2005).
Sinclair et al., "Glycoengineering: the effect of glycosylation on the properties of therapeutic proteins," *J. Pharm. Sci.* 94: 1626-1635 (2005).

(Continued)

*Primary Examiner* — Padma V Baskar
(74) *Attorney, Agent, or Firm* — Clark & Elbing LLP; Kristina Bieker-Brady

(57) ABSTRACT

*Chlamydia* antigens (e.g., polypeptides, polypeptide fragments, and fusion proteins) are provided. Also provided are vaccines and pharmaceutical compositions for treating or preventing a bacterial infection, such as *Chlamydia*, in a subject.

8 Claims, 11 Drawing Sheets

(56) References Cited

OTHER PUBLICATIONS

Stephens et al., "Genome sequence of an obligate intracellular pathogen of humans: *Chlamydia trachomatis*," *Science* 282: 754-759 (1998).

Su et al., "Protective efficacy of a parenterally administered MOMP-derived synthetic oligopeptide vaccine in a murine model of *Chlamydia trachomatis* genital tract infection: serum neutralizing IgG antibodies do not protect against chlamydial genital tract infection," *Vaccine* 13: 1023-1032 (1995).

Taylor et al., "Oral immunization with chlamydial major outer membrane protein (MOMP)," *Invest. Ophthalmol. Vis. Sci.* 29: 1847-1853 (1988).

Weinberg et al., "Selective depletion of myelin-reactive T cells with the anti-OX-40 antibody ameliorates autoimmune encephalomyelitis," *Nat. Med.* 2: 183-189 (1996).

Zhang et al., "DNA vaccination with the major outer-membrane protein gene induces acquired immunity to *Chlamydia trachomatis* (mouse pneumonitis) infection," *J. Infect. Dis.* 176: 1035-1040 (1997).

Supplementary European Search Report from European Application No. 08856184.0, search completed May 26, 2011, Search Report mailed Jun. 6, 2011.

EPO Communication for European Patent Application No. 08856184.0, dated Jun. 26, 2013 (4 pages).

* cited by examiner

FIGURE 1

CT491 (SEQ ID NO: 1)

```
  1 mkeespaevl qkvkehkrre gplslekevs edsavateek
 41 etsqpvavtk iaklqrmgin elnvlarqyg vknvgsltks
 81 qvvfeivkak serpdeflig egvlevlpdg fgflrsptyn
121 ylpsaediyv spaqirrfdl kkgdtivgti rspkekekyf
161 allkvdking stpdkakerv lfenltplhp nerlimemgk
201 enlaervldl tapigkgqrg livapprsgk tvilqsiaha
241 iavnnpdael ivllidepre evtdmirqvr gevvastfde
281 qpdrhiqvte mviekarrlv ehgkdvvill dsitrlaray
321 ntvqphsgki ltggvdasal hkpkrffgaa rniegggslt
361 ilatalidtg srmdevifee fkgtgnmelv ldrhlsdrri
401 ypaidliksg trkeellyhp gelekirlfr qaiagltaid
441 amhlllgrlk ktnsntefll slkd
```

FIGURE 2

CT601 (SEQ ID NO: 2)

```
  1 mlanrlflit llglsssvyg agkapslqai laevedtssr
 41 lhahhnelam iserldeqdt klqqlsstqd hnlprqvqrl
 81 etdqkalakt lailsqsvqd irssvqnklq eiqqeqkkla
121 qnlralrnsl qalvdgsspe nyidfltget pehihivkqg
161 etlskiasky nipvvelkkl nklnsdtift dqrirlpkkk
```

FIGURE 3

CT687 (SEQ ID NO: 3)

```
  1 mynvkkdfpi fknqgdpyvy ldsaatthkp qcvidsivdy
 41 ysssyatvnr alytashdit fahwqvrskv gswigaqydq
 81 eiiftrgtts slnllaiaan dswlaggtvv iseaehhanl
121 vswelacqrs gatikkvrvd degmvdcshl eqllkqgvql
161 vslahvsnvs gavlplpeia hlvhryealf avdgaqgvgk
201 gplnlsewgv dfyafsghkl yaptgigvly gkkelleslp
241 pvegggdmvi vydfeelsyq epplrfeagt phiagvlglg
281 aaidylqalp fsitdrltel thflyeqllt vpgiqiigpk
321 qgaargslcs isipgvqasd lgflldgrgi svrsghqcsq
361 pamvrwdlgh vlraslgiyn eqqdillfve alkdilrayr
401 s
```

FIGURE 4

CT732 (SEQ ID NO: 4)

```
  1  mkplkgcpva  kdvrvaivgs  cfnspiadrl  vagaqetffd
 41  fggdpsslti  vrvpgafeip  caikkllsts  gqfhavvacg
 81  vliqgetshy  ehiadsvaag  vsrlsldfcl  pitfsvitap
121  nmeaawerag  ikgpnlgasg  mktalemasl  fsligke
```

FIGURE 5

CT781 (SEQ ID NO: 5)

```
  1  msveveylqh edylyrtskl keirdlginp ypyqytdcle
 41  vqeirnqfvd nelgdseaaf rketpkvrfa grlvlfrsmg
 81  knsfgqildn dakiqvmfnr dfsavaglaa dagispikfi
121  ekkldlgdil glegylffth sgeltvlvet vtllckslis
161  lpdkhaglad keiryrkrwa dlissedvrk tfltrsrilk
201  lireymdqqs flevetpilq tiyggaeatp fvttlqalha
241  emflrislei alkkllvggm srvyeigkvf rnegidrthn
281  peftmieaya aywdyndvmk cvenlveyiv ralnngetqv
321  qyshlksgpq vvdfkapwir mtmkesisvy ggvdvdlhad
361  helrkiletq tslpektyvh asrgeliall fdelvcdkli
401  aphhitdhpl ettplcktlr sgdetlverf esfclgkelc
441  nayselndpl qqrklleeqm rkkalnpdse yhpideefle
481  alcqgmppag gfgigidrlv mmltdaasir dvlffpvmrr
521  ieakkd
```

FIGURE 6

CT808 (SEQ ID NO: 6)

```
  1 mendillnie skeiryahlk ngqlfdliie rkkirqlkgn
 41 iyrgrvtnil rniqsafini derengfihi sdvlenskkf
 81 eqmfdidsda dhaepqpeet skapieellk ldspvlqvv
121 kepigtkgar ltsnisipgr ylvllpnsph rgvsrkiedp
161 lmrdqlkqli rsfempqnmg licrtasisa stetlineaq
201 dllntwqsil ekfyspdhps llyeetdilk kavmtcvdks
241 ykrlliddya tyqkckrllg kyspdttvki eyyrdsvpmf
281 erfniekeid ratkrkiwls sggylffdkt eamhtidvns
321 grstqlengv eetlvqinle aaeeiarqlr lnigglvii
361 dfidmksrkn qrrvlerlke hmkydaarct ilsmsefglv
401 emtrqrnres lmqtlfttcp ycngnaiikt sesilieier
441 dlkkiikhke htnlclvvhp eiahymkqeq ddvelirlak
481 qlkaklqint sdsihlnhyq ffslitgegi el
```

FIGURE 7

CT823 (SEQ ID NO: 7)

```
  1 mmkrllcvll stsvfsspml gysaskkdsk adiclavssg
 41 dqevsqedll kevsrgfsrv aakatpgvvy ienfpktgnq
 81 aiaspgnkrg fqenpfdyfn deffnrffgl pshreqqrpq
121 qrdavrgtgf ivsedgyvvt nhhvvedagk ihvtlhdgqk
161 ytakivgldp ktdlavikiq aeklpfltfg nsdqlqigdw
201 aiaignpfgl qatvtgvis akgrnqlhiv dfedfiqtda
241 ainpgnsggp llningqvig vntaivsgsg gyigigfaip
281 slmakrvidq lisdgqvtrg flgvtlqpid selatcykle
321 kvygalvtdv vkgspaekag lrqedvivay ngkeveslsa
361 lrnaislmmp gtrvvlkivr egktieipvt vtqiptedgv
401 salqkmgvrv qnitpeickk lglaadtrgi lvvaveagsp
441 aasagvapgq lilavnrqrv asveelnqvl knskgenvll
481 mvsqgdvvrf ivlksde
```

FIGURE 8

CT062 (SEQ ID NO: 8)

```
  1 mqqlidnlkk rgildnssag lesltvpvsa ylgfdptaps
 41 lhighwigic flrrlaaygi tpvalvggat gmigdpsgks
 61 verslldqaq vldnskkiaa alasylpgir ivnnadwlgs
121 lsmvdflrdv gkhfrlgsml akdvvkqrvy seegisytef
161 sylllqsydf ahlfkehnvv lqcggsdqwg nitsgidyir
201 rrglgqaygl typlltdskg kkigktesgt iwldpaltpp
241 yelfqyflrl pdqeiskvmr tltlldneei falderltsd
281 pqavkkyiae vivkdvhgse glaqaqaate sffaskgksi
321 teaelvalve sgvgvkvara dligkrwldi vvelgfcssr
361 gqarrliqqr glyinqepla deqsildgtq lcfdryvlls
401 qgkrkkqvid ln
```

FIGURE 9

Partial Amino Acid Sequence of CT062 (SEQ ID NO: 9)
(Amino Acids 23-412 of Genebank Accession No. NP_219565)

```
  1 sltvpvsayl gfdptapslh ighwigicfl rrlaaygitp
 41 valvggatgm igdpsgksve rslldqaqvl dnskkiaaal
 81 asylpgiriv nnadwlgsls mvdflrdvgk hfrlgsmlak
121 dvvkqrvyse egisytefsy lllqsydfah lfkehnvvlq
161 cggsdqwgni tsgidyirrr glgqayglty plltdskgkk
201 igktesgtiw ldpaltppye lfqyflrlpd qeiskvmrtl
241 tlldneeifa lderltsdpq avkkyiaevi vkdvhgsegl
281 aqaqaatesf faskgksite aelvalvesg vgvkvaradl
321 igkrwldivv elgfcssrgq arrliqqrgl yinqeplade
361 qsildgtqlc fdryvllsqg krkkqvidln
```

FIGURE 10

CT104 (SEQ ID NO: 10)

```
  1  mlkidltgki  afiagigddn  gygwgiakml  aeagatilvg
 41  twvpiykifs  qslelgkfna  srelsngell  tfakiypmda
 81  sfdtpedipq  eilenkrykd  lsgytvsevv  eqvkkhfghi
121  dilvhslans  peiakplldt  srkgylaals  tssysfisll
161  shfgpimnag  astisltyla  smravpgygg  gmnaakaale
201  sdtkvlawea  grrwgvrvnt  isagplasra  gkaigfierm
241  vdyyqdwapl  pspmeaeqvg  aaaaflvspl  asaitgetly
281  vdhganvmgi  gpemfpkd
```

FIGURE 11

CT111 (SEQ ID NO: 11)

```
 1 msdqattlki kplgdrilvk reeeastarg giilpdtakk
41 kqdraevlal gtgkkddkgq qlpfevqvgn ivlidkysgq
81 eltvegeeyv ivqmseviav lq
```

SEQUENCE LISTING

```
<160> NUMBER OF SEQ ID NOS: 14

<210> SEQ ID NO 1
<211> LENGTH: 464
<212> TYPE: PRT
<213> ORGANISM: Chlamydia trachomatis

<400> SEQUENCE: 1
```

```
Met Lys Glu Glu Ser Pro Ala Glu Val Leu Gln Lys Val Lys Glu His
1               5                   10                  15

Lys Arg Arg Glu Gly Pro Leu Ser Leu Glu Lys Glu Val Ser Glu Asp
                20                  25                  30

Ser Ala Val Ala Thr Glu Glu Lys Glu Thr Ser Gln Pro Val Ala Val
                35                  40                  45

Thr Lys Ile Ala Lys Leu Gln Arg Met Gly Ile Asn Glu Leu Asn Val
            50                  55                  60

Leu Ala Arg Gln Tyr Gly Val Lys Asn Val Gly Ser Leu Thr Lys Ser
65                  70                  75                  80

Gln Val Val Phe Glu Ile Val Lys Ala Lys Ser Glu Arg Pro Asp Glu
                85                  90                  95

Phe Leu Ile Gly Glu Gly Val Leu Glu Val Leu Pro Asp Gly Phe Gly
                100                 105                 110

Phe Leu Arg Ser Pro Thr Tyr Asn Tyr Leu Pro Ser Ala Glu Asp Ile
                115                 120                 125

Tyr Val Ser Pro Ala Gln Ile Arg Arg Phe Asp Leu Lys Lys Gly Asp
                130                 135                 140

Thr Ile Val Gly Thr Ile Arg Ser Pro Lys Glu Lys Glu Lys Tyr Phe
145                 150                 155                 160

Ala Leu Leu Lys Val Asp Lys Ile Asn Gly Ser Thr Pro Asp Lys Ala
                165                 170                 175

Lys Glu Arg Val Leu Phe Glu Asn Leu Thr Pro Leu His Pro Asn Glu
                180                 185                 190

Arg Leu Ile Met Glu Met Gly Lys Glu Asn Leu Ala Glu Arg Val Leu
                195                 200                 205

Asp Leu Thr Ala Pro Ile Gly Lys Gly Gln Arg Gly Leu Ile Val Ala
                210                 215                 220

Pro Pro Arg Ser Gly Lys Thr Val Ile Leu Gln Ser Ile Ala His Ala
225                 230                 235                 240

Ile Ala Val Asn Asn Pro Asp Ala Glu Leu Ile Val Leu Leu Ile Asp
                245                 250                 255

Glu Arg Pro Glu Glu Val Thr Asp Met Ile Arg Gln Val Arg Gly Glu
                260                 265                 270

Val Val Ala Ser Thr Phe Asp Glu Gln Pro Asp Arg His Ile Gln Val
                275                 280                 285

Thr Glu Met Val Ile Glu Lys Ala Arg Arg Leu Val Glu His Gly Lys
                290                 295                 300

Asp Val Val Ile Leu Leu Asp Ser Ile Thr Arg Leu Ala Arg Ala Tyr
305                 310                 315                 320

Asn Thr Val Gln Pro His Ser Gly Lys Ile Leu Thr Gly Gly Val Asp
                325                 330                 335

Ala Ser Ala Leu His Lys Pro Lys Arg Phe Phe Gly Ala Ala Arg Asn
                340                 345                 350

Ile Glu Gly Gly Gly Ser Leu Thr Ile Leu Ala Thr Ala Leu Ile Asp
                355                 360                 365

Thr Gly Ser Arg Met Asp Glu Val Ile Phe Glu Glu Phe Lys Gly Thr
                370                 375                 380

Gly Asn Met Glu Leu Val Leu Asp Arg His Leu Ser Asp Arg Arg Ile
385                 390                 395                 400

Tyr Pro Ala Ile Asp Leu Ile Lys Ser Gly Thr Arg Lys Glu Glu Leu
                405                 410                 415

Leu Tyr His Pro Gly Glu Leu Glu Lys Ile Arg Leu Phe Arg Gln Ala
                420                 425                 430
```

```
Ile Ala Gly Leu Thr Ala Ile Asp Ala Met His Leu Leu Gly Arg
        435                 440                 445

Leu Lys Lys Thr Asn Ser Asn Thr Glu Phe Leu Leu Ser Leu Lys Asp
        450                 455                 460

<210> SEQ ID NO 2
<211> LENGTH: 200
<212> TYPE: PRT
<213> ORGANISM: Chlamydia trachomatis

<400> SEQUENCE: 2

Met Leu Ala Asn Arg Leu Phe Leu Ile Thr Leu Gly Leu Ser Ser
1               5                   10                  15

Ser Val Tyr Gly Ala Gly Lys Ala Pro Ser Leu Gln Ala Ile Leu Ala
            20                  25                  30

Glu Val Glu Asp Thr Ser Ser Arg Leu His Ala His Asn Glu Leu
        35                  40                  45

Ala Met Ile Ser Glu Arg Leu Asp Glu Gln Asp Thr Lys Leu Gln Gln
    50                  55                  60

Leu Ser Ser Thr Gln Asp His Asn Leu Pro Arg Gln Val Gln Arg Leu
65                  70                  75                  80

Glu Thr Asp Gln Lys Ala Leu Ala Lys Thr Leu Ala Ile Leu Ser Gln
                85                  90                  95

Ser Val Gln Asp Ile Arg Ser Ser Val Gln Asn Lys Leu Gln Glu Ile
            100                 105                 110

Gln Gln Glu Gln Lys Lys Leu Ala Gln Asn Leu Arg Ala Leu Arg Asn
        115                 120                 125

Ser Leu Gln Ala Leu Val Asp Gly Ser Ser Pro Glu Asn Tyr Ile Asp
    130                 135                 140

Phe Leu Thr Gly Glu Thr Pro Glu His Ile His Ile Val Lys Gln Gly
145                 150                 155                 160

Glu Thr Leu Ser Lys Ile Ala Ser Lys Tyr Asn Ile Pro Val Val Glu
                165                 170                 175

Leu Lys Lys Leu Asn Lys Leu Asn Ser Asp Thr Ile Phe Thr Asp Gln
            180                 185                 190

Arg Ile Arg Leu Pro Lys Lys Lys
        195                 200

<210> SEQ ID NO 3
<211> LENGTH: 401
<212> TYPE: PRT
<213> ORGANISM: Chlamydia trachomatis

<400> SEQUENCE: 3

Met Tyr Asn Val Lys Lys Asp Phe Pro Ile Phe Lys Asn Gln Gly Asp
1               5                   10                  15

Pro Tyr Val Tyr Leu Asp Ser Ala Thr Thr His Lys Pro Gln Cys
            20                  25                  30

Val Ile Asp Ser Ile Val Asp Tyr Tyr Ser Ser Ser Tyr Ala Thr Val
        35                  40                  45

Asn Arg Ala Leu Tyr Thr Ala Ser His Asp Ile Thr Phe Ala His Trp
    50                  55                  60

Gln Val Arg Ser Lys Val Gly Ser Trp Ile Gly Ala Gln Tyr Asp Gln
65                  70                  75                  80

Glu Ile Ile Phe Thr Arg Gly Thr Thr Ser Ser Leu Asn Leu Leu Ala
                85                  90                  95
```

```
Ile Ala Ala Asn Asp Ser Trp Leu Ala Gly Gly Thr Val Val Ile Ser
            100                 105                 110

Glu Ala Glu His His Ala Asn Leu Val Ser Trp Glu Leu Ala Cys Gln
        115                 120                 125

Arg Ser Gly Ala Thr Ile Lys Lys Val Arg Val Asp Asp Glu Gly Met
130                 135                 140

Val Asp Cys Ser His Leu Glu Gln Leu Leu Lys Gln Gly Val Gln Leu
145                 150                 155                 160

Val Ser Leu Ala His Val Ser Asn Val Ser Gly Ala Val Leu Pro Leu
                165                 170                 175

Pro Glu Ile Ala His Leu Val His Arg Tyr Glu Ala Leu Phe Ala Val
            180                 185                 190

Asp Gly Ala Gln Gly Val Gly Lys Gly Pro Leu Asn Leu Ser Glu Trp
        195                 200                 205

Gly Val Asp Phe Tyr Ala Phe Ser Gly His Lys Leu Tyr Ala Pro Thr
210                 215                 220

Gly Ile Gly Val Leu Tyr Gly Lys Lys Glu Leu Leu Glu Ser Leu Pro
225                 230                 235                 240

Pro Val Glu Gly Gly Gly Asp Met Val Ile Val Tyr Asp Phe Glu Glu
                245                 250                 255

Leu Ser Tyr Gln Glu Pro Pro Leu Arg Phe Glu Ala Gly Thr Pro His
            260                 265                 270

Ile Ala Gly Val Leu Gly Leu Gly Ala Ala Ile Asp Tyr Leu Gln Ala
        275                 280                 285

Leu Pro Phe Ser Ile Thr Asp Arg Leu Thr Glu Leu Thr His Phe Leu
290                 295                 300

Tyr Glu Gln Leu Leu Thr Val Pro Gly Ile Gln Ile Ile Gly Pro Lys
305                 310                 315                 320

Gln Gly Ala Ala Arg Gly Ser Leu Cys Ser Ile Ser Ile Pro Gly Val
                325                 330                 335

Gln Ala Ser Asp Leu Gly Phe Leu Leu Asp Gly Arg Gly Ile Ser Val
            340                 345                 350

Arg Ser Gly His Gln Cys Ser Gln Pro Ala Met Val Arg Trp Asp Leu
        355                 360                 365

Gly His Val Leu Arg Ala Ser Leu Gly Ile Tyr Asn Glu Gln Gln Asp
370                 375                 380

Ile Leu Leu Phe Val Glu Ala Leu Lys Asp Ile Leu Arg Ala Tyr Arg
385                 390                 395                 400

Ser

<210> SEQ ID NO 4
<211> LENGTH: 157
<212> TYPE: PRT
<213> ORGANISM: Chlamydia Trachomatis

<400> SEQUENCE: 4

Met Lys Pro Leu Lys Gly Cys Pro Val Ala Lys Asp Val Arg Val Ala
1               5                   10                  15

Ile Val Gly Ser Cys Phe Asn Ser Pro Ile Ala Asp Arg Leu Val Ala
            20                  25                  30

Gly Ala Gln Glu Thr Phe Phe Asp Phe Gly Asp Pro Ser Ser Leu
        35                  40                  45

Thr Ile Val Arg Val Pro Gly Ala Phe Glu Ile Pro Cys Ala Ile Lys
50                  55                  60

Lys Leu Leu Ser Thr Ser Gly Gln Phe His Ala Val Val Ala Cys Gly
```

```
                65                  70                  75                  80
Val Leu Ile Gln Gly Glu Thr Ser His Tyr Glu His Ile Ala Asp Ser
                    85                  90                  95

Val Ala Ala Gly Val Ser Arg Leu Ser Leu Asp Phe Cys Leu Pro Ile
                100                 105                 110

Thr Phe Ser Val Ile Thr Ala Pro Asn Met Glu Ala Ala Trp Glu Arg
            115                 120                 125

Ala Gly Ile Lys Gly Pro Asn Leu Gly Ala Ser Gly Met Lys Thr Ala
        130                 135                 140

Leu Glu Met Ala Ser Leu Phe Ser Leu Ile Gly Lys Glu
145                 150                 155

<210> SEQ ID NO 5
<211> LENGTH: 526
<212> TYPE: PRT
<213> ORGANISM: Chlamydia trachomatis

<400> SEQUENCE: 5

Met Ser Val Glu Val Glu Tyr Leu Gln His Glu Asp Tyr Leu Tyr Arg
1               5                   10                  15

Thr Ser Lys Leu Lys Glu Ile Arg Asp Leu Gly Ile Asn Pro Tyr Pro
                20                  25                  30

Tyr Gln Tyr Thr Asp Cys Leu Glu Val Gln Glu Ile Arg Asn Gln Phe
            35                  40                  45

Val Asp Asn Glu Leu Gly Asp Ser Glu Ala Ala Phe Arg Lys Glu Thr
        50                  55                  60

Pro Lys Val Arg Phe Ala Gly Arg Leu Val Leu Phe Arg Ser Met Gly
65                  70                  75                  80

Lys Asn Ser Phe Gly Gln Ile Leu Asp Asn Asp Ala Lys Ile Gln Val
                85                  90                  95

Met Phe Asn Arg Asp Phe Ser Ala Val Ala Gly Leu Ala Ala Asp Ala
            100                 105                 110

Gly Ile Ser Pro Ile Lys Phe Ile Glu Lys Lys Leu Asp Leu Gly Asp
        115                 120                 125

Ile Leu Gly Leu Glu Gly Tyr Leu Phe Phe Thr His Ser Gly Glu Leu
    130                 135                 140

Thr Val Leu Val Glu Thr Val Thr Leu Leu Cys Lys Ser Leu Ile Ser
145                 150                 155                 160

Leu Pro Asp Lys His Ala Gly Leu Ala Asp Lys Glu Ile Arg Tyr Arg
                165                 170                 175

Lys Arg Trp Ala Asp Leu Ile Ser Ser Glu Asp Val Arg Lys Thr Phe
            180                 185                 190

Leu Thr Arg Ser Arg Ile Leu Lys Leu Ile Arg Glu Tyr Met Asp Gln
        195                 200                 205

Gln Ser Phe Leu Glu Val Glu Thr Pro Ile Leu Gln Thr Ile Tyr Gly
    210                 215                 220

Gly Ala Glu Ala Thr Pro Phe Val Thr Thr Leu Gln Ala Leu His Ala
225                 230                 235                 240

Glu Met Phe Leu Arg Ile Ser Leu Glu Ile Ala Leu Lys Lys Leu Leu
                245                 250                 255

Val Gly Gly Met Ser Arg Val Tyr Glu Ile Gly Lys Val Phe Arg Asn
            260                 265                 270

Glu Gly Ile Asp Arg Thr His Asn Pro Glu Phe Thr Met Ile Glu Ala
        275                 280                 285

Tyr Ala Ala Tyr Trp Asp Tyr Asn Asp Val Met Lys Cys Val Glu Asn
```

```
            290                 295                 300
Leu Val Glu Tyr Ile Val Arg Ala Leu Asn Asn Gly Glu Thr Gln Val
305                 310                 315                 320

Gln Tyr Ser His Leu Lys Ser Gly Pro Gln Val Val Asp Phe Lys Ala
                325                 330                 335

Pro Trp Ile Arg Met Thr Met Lys Glu Ser Ile Ser Val Tyr Gly Gly
                340                 345                 350

Val Asp Val Asp Leu His Ala Asp His Glu Leu Arg Lys Ile Leu Glu
                355                 360                 365

Thr Gln Thr Ser Leu Pro Glu Lys Thr Tyr Val His Ala Ser Arg Gly
370                 375                 380

Glu Leu Ile Ala Leu Leu Phe Asp Glu Leu Val Cys Asp Lys Leu Ile
385                 390                 395                 400

Ala Pro His His Ile Thr Asp His Pro Leu Glu Thr Thr Pro Leu Cys
                405                 410                 415

Lys Thr Leu Arg Ser Gly Asp Glu Thr Leu Val Glu Arg Phe Glu Ser
                420                 425                 430

Phe Cys Leu Gly Lys Glu Leu Cys Asn Ala Tyr Ser Glu Leu Asn Asp
                435                 440                 445

Pro Leu Gln Gln Arg Lys Leu Leu Glu Glu Gln Met Arg Lys Lys Ala
                450                 455                 460

Leu Asn Pro Asp Ser Glu Tyr His Pro Ile Asp Glu Phe Leu Glu
465                 470                 475                 480

Ala Leu Cys Gln Gly Met Pro Pro Ala Gly Gly Phe Gly Ile Gly Ile
                485                 490                 495

Asp Arg Leu Val Met Met Leu Thr Asp Ala Ala Ser Ile Arg Asp Val
                500                 505                 510

Leu Phe Phe Pro Val Met Arg Arg Ile Glu Ala Lys Lys Asp
                515                 520                 525

<210> SEQ ID NO 6
<211> LENGTH: 512
<212> TYPE: PRT
<213> ORGANISM: Chlamydia trachomatis

<400> SEQUENCE: 6

Met Glu Asn Asp Ile Leu Leu Asn Ile Glu Ser Lys Glu Ile Arg Tyr
1               5                   10                  15

Ala His Leu Lys Asn Gly Gln Leu Phe Asp Leu Ile Ile Glu Arg Lys
                20                  25                  30

Lys Ile Arg Gln Leu Lys Gly Asn Ile Tyr Arg Gly Arg Val Thr Asn
                35                  40                  45

Ile Leu Arg Asn Ile Gln Ser Ala Phe Ile Asn Ile Asp Glu Arg Glu
                50                  55                  60

Asn Gly Phe Ile His Ile Ser Asp Val Leu Glu Asn Ser Lys Lys Phe
65              70                  75                  80

Glu Gln Met Phe Asp Ile Asp Ser Asp Ala Asp His Ala Glu Pro Gln
                85                  90                  95

Pro Glu Glu Thr Ser Lys Ala Pro Ile Glu Glu Leu Leu Lys Leu Asp
                100                 105                 110

Ser Pro Val Leu Val Gln Val Val Lys Glu Pro Ile Gly Thr Lys Gly
                115                 120                 125

Ala Arg Leu Thr Ser Asn Ile Ser Ile Pro Gly Arg Tyr Leu Val Leu
                130                 135                 140

Leu Pro Asn Ser Pro His Arg Gly Val Ser Arg Lys Ile Glu Asp Pro
```

```
                145                 150                 155                 160
Leu Met Arg Asp Gln Leu Lys Gln Leu Ile Arg Ser Phe Glu Met Pro
                    165                 170                 175

Gln Asn Met Gly Leu Ile Cys Arg Thr Ala Ser Ile Ser Ala Ser Thr
                180                 185                 190

Glu Thr Leu Ile Asn Glu Ala Gln Asp Leu Leu Asn Thr Trp Gln Ser
                195                 200                 205

Ile Leu Glu Lys Phe Tyr Ser Pro Asp His Pro Ser Leu Leu Tyr Glu
            210                 215                 220

Glu Thr Asp Ile Leu Lys Lys Ala Val Met Thr Cys Val Asp Lys Ser
225                 230                 235                 240

Tyr Lys Arg Leu Leu Ile Asp Asp Tyr Ala Thr Tyr Gln Lys Cys Lys
                245                 250                 255

Arg Leu Leu Gly Lys Tyr Ser Pro Asp Thr Thr Val Lys Ile Glu Tyr
                260                 265                 270

Tyr Arg Asp Ser Val Pro Met Phe Glu Arg Phe Asn Ile Glu Lys Glu
            275                 280                 285

Ile Asp Arg Ala Thr Lys Arg Lys Ile Trp Leu Ser Ser Gly Gly Tyr
        290                 295                 300

Leu Phe Phe Asp Lys Thr Glu Ala Met His Thr Ile Asp Val Asn Ser
305                 310                 315                 320

Gly Arg Ser Thr Gln Leu Glu Asn Gly Val Glu Glu Thr Leu Val Gln
                325                 330                 335

Ile Asn Leu Glu Ala Ala Glu Glu Ile Ala Arg Gln Leu Arg Leu Arg
            340                 345                 350

Asn Ile Gly Gly Leu Val Ile Ile Asp Phe Ile Asp Met Lys Ser Arg
        355                 360                 365

Lys Asn Gln Arg Arg Val Leu Glu Arg Leu Lys Glu His Met Lys Tyr
    370                 375                 380

Asp Ala Ala Arg Cys Thr Ile Leu Ser Met Ser Glu Phe Gly Leu Val
385                 390                 395                 400

Glu Met Thr Arg Gln Arg Asn Arg Glu Ser Leu Met Gln Thr Leu Phe
                405                 410                 415

Thr Thr Cys Pro Tyr Cys Asn Gly Asn Ala Ile Ile Lys Thr Ser Glu
                420                 425                 430

Ser Ile Leu Ile Glu Ile Glu Arg Asp Leu Lys Lys Ile Ile Lys His
            435                 440                 445

Lys Glu His Thr Asn Leu Cys Leu Val Val His Pro Glu Ile Ala His
    450                 455                 460

Tyr Met Lys Gln Glu Gln Asp Asp Val Glu Leu Ile Arg Leu Ala Lys
465                 470                 475                 480

Gln Leu Lys Ala Lys Leu Gln Ile Asn Thr Ser Asp Ser Ile His Leu
                485                 490                 495

Asn His Tyr Gln Phe Phe Ser Leu Ile Thr Gly Glu Gly Ile Glu Leu
                500                 505                 510

<210> SEQ ID NO 7
<211> LENGTH: 497
<212> TYPE: PRT
<213> ORGANISM: Chlamydia trachomatis

<400> SEQUENCE: 7

Met Met Lys Arg Leu Leu Cys Val Leu Leu Ser Thr Ser Val Phe Ser
1               5                   10                  15

Ser Pro Met Leu Gly Tyr Ser Ala Ser Lys Lys Asp Ser Lys Ala Asp
```

```
                     20                  25                  30
Ile Cys Leu Ala Val Ser Ser Gly Asp Gln Glu Val Ser Gln Glu Asp
         35                  40                  45

Leu Leu Lys Glu Val Ser Arg Gly Phe Ser Arg Val Ala Ala Lys Ala
 50                  55                  60

Thr Pro Gly Val Val Tyr Ile Glu Asn Phe Pro Lys Thr Gly Asn Gln
 65                      70                  75                  80

Ala Ile Ala Ser Pro Gly Asn Lys Arg Gly Phe Gln Glu Asn Pro Phe
                 85                  90                  95

Asp Tyr Phe Asn Asp Glu Phe Phe Asn Arg Phe Phe Gly Leu Pro Ser
                100                 105                 110

His Arg Glu Gln Gln Arg Pro Gln Gln Arg Asp Ala Val Arg Gly Thr
             115                 120                 125

Gly Phe Ile Val Ser Glu Asp Gly Tyr Val Val Thr Asn His His Val
         130                 135                 140

Val Glu Asp Ala Gly Lys Ile His Val Thr Leu His Asp Gly Gln Lys
145                 150                 155                 160

Tyr Thr Ala Lys Ile Val Gly Leu Asp Pro Lys Thr Asp Leu Ala Val
                 165                 170                 175

Ile Lys Ile Gln Ala Glu Lys Leu Pro Phe Leu Thr Phe Gly Asn Ser
             180                 185                 190

Asp Gln Leu Gln Ile Gly Asp Trp Ala Ile Ala Ile Gly Asn Pro Phe
         195                 200                 205

Gly Leu Gln Ala Thr Val Thr Val Gly Val Ile Ser Ala Lys Gly Arg
     210                 215                 220

Asn Gln Leu His Ile Val Asp Phe Glu Asp Phe Ile Gln Thr Asp Ala
225                 230                 235                 240

Ala Ile Asn Pro Gly Asn Ser Gly Gly Pro Leu Leu Asn Ile Asn Gly
                 245                 250                 255

Gln Val Ile Gly Val Asn Thr Ala Ile Val Ser Gly Ser Gly Gly Tyr
             260                 265                 270

Ile Gly Ile Gly Phe Ala Ile Pro Ser Leu Met Ala Lys Arg Val Ile
         275                 280                 285

Asp Gln Leu Ile Ser Asp Gly Gln Val Thr Arg Gly Phe Leu Gly Val
     290                 295                 300

Thr Leu Gln Pro Ile Asp Ser Glu Leu Ala Thr Cys Tyr Lys Leu Glu
305                 310                 315                 320

Lys Val Tyr Gly Ala Leu Val Thr Asp Val Lys Gly Ser Pro Ala
                 325                 330                 335

Glu Lys Ala Gly Leu Arg Gln Glu Asp Val Ile Val Ala Tyr Asn Gly
             340                 345                 350

Lys Glu Val Glu Ser Leu Ser Ala Leu Arg Asn Ala Ile Ser Leu Met
         355                 360                 365

Met Pro Gly Thr Arg Val Val Leu Lys Ile Val Arg Glu Gly Lys Thr
     370                 375                 380

Ile Glu Ile Pro Val Thr Val Thr Gln Ile Pro Thr Glu Asp Gly Val
385                 390                 395                 400

Ser Ala Leu Gln Lys Met Gly Val Arg Val Gln Asn Ile Thr Pro Glu
                 405                 410                 415

Ile Cys Lys Lys Leu Gly Leu Ala Ala Asp Thr Arg Gly Ile Leu Val
             420                 425                 430

Val Ala Val Glu Ala Gly Ser Pro Ala Ala Ser Ala Gly Val Ala Pro
         435                 440                 445
```

```
Gly Gln Leu Ile Leu Ala Val Asn Arg Gln Arg Val Ala Ser Val Glu
            450                 455                 460
Glu Leu Asn Gln Val Leu Lys Asn Ser Lys Gly Glu Asn Val Leu Leu
465                 470                 475                 480
Met Val Ser Gln Gly Asp Val Val Arg Phe Ile Val Leu Lys Ser Asp
                485                 490                 495
Glu

<210> SEQ ID NO 8
<211> LENGTH: 412
<212> TYPE: PRT
<213> ORGANISM: Chlamydia trachomatis

<400> SEQUENCE: 8

Met Gln Gln Leu Ile Asp Asn Leu Lys Lys Arg Gly Ile Leu Asp Asn
1               5                   10                  15
Ser Ser Ala Gly Leu Glu Ser Leu Thr Val Pro Val Ser Ala Tyr Leu
            20                  25                  30
Gly Phe Asp Pro Thr Ala Pro Ser Leu His Ile Gly His Trp Ile Gly
        35                  40                  45
Ile Cys Phe Leu Arg Arg Leu Ala Ala Tyr Gly Ile Thr Pro Val Ala
    50                  55                  60
Leu Val Gly Gly Ala Thr Gly Met Ile Gly Asp Pro Ser Gly Lys Ser
65                  70                  75                  80
Val Glu Arg Ser Leu Leu Asp Gln Ala Gln Val Leu Asp Asn Ser Lys
                85                  90                  95
Lys Ile Ala Ala Ala Leu Ala Ser Tyr Leu Pro Gly Ile Arg Ile Val
            100                 105                 110
Asn Asn Ala Asp Trp Leu Gly Ser Leu Ser Met Val Asp Phe Leu Arg
        115                 120                 125
Asp Val Gly Lys His Phe Arg Leu Gly Ser Met Leu Ala Lys Asp Val
    130                 135                 140
Val Lys Gln Arg Val Tyr Ser Glu Glu Gly Ile Ser Tyr Thr Glu Phe
145                 150                 155                 160
Ser Tyr Leu Leu Leu Gln Ser Tyr Asp Phe Ala His Leu Phe Lys Glu
                165                 170                 175
His Asn Val Val Leu Gln Cys Gly Gly Ser Asp Gln Trp Gly Asn Ile
            180                 185                 190
Thr Ser Gly Ile Asp Tyr Ile Arg Arg Gly Leu Gly Gln Ala Tyr
        195                 200                 205
Gly Leu Thr Tyr Pro Leu Leu Thr Asp Ser Lys Gly Lys Lys Ile Gly
    210                 215                 220
Lys Thr Glu Ser Gly Thr Ile Trp Leu Asp Pro Ala Leu Thr Pro Pro
225                 230                 235                 240
Tyr Glu Leu Phe Gln Tyr Phe Leu Arg Leu Pro Asp Gln Glu Ile Ser
                245                 250                 255
Lys Val Met Arg Thr Leu Thr Leu Leu Asp Asn Glu Glu Ile Phe Ala
            260                 265                 270
Leu Asp Glu Arg Leu Thr Ser Asp Pro Gln Ala Val Lys Lys Tyr Ile
        275                 280                 285
Ala Glu Val Ile Val Lys Asp Val His Gly Ser Glu Gly Leu Ala Gln
    290                 295                 300
Ala Gln Ala Ala Thr Glu Ser Phe Phe Ala Ser Lys Gly Lys Ser Ile
305                 310                 315                 320
Thr Glu Ala Glu Leu Val Ala Leu Val Glu Ser Gly Val Gly Val Lys
```

```
                    325                 330                 335
Val Ala Arg Ala Asp Leu Ile Gly Lys Arg Trp Leu Asp Ile Val Val
            340                 345                 350

Glu Leu Gly Phe Cys Ser Ser Arg Gly Gln Ala Arg Arg Leu Ile Gln
            355                 360                 365

Gln Arg Gly Leu Tyr Ile Asn Gln Glu Pro Leu Ala Asp Glu Gln Ser
        370                 375                 380

Ile Leu Asp Gly Thr Gln Leu Cys Phe Asp Arg Tyr Val Leu Leu Ser
385                 390                 395                 400

Gln Gly Lys Arg Lys Lys Gln Val Ile Asp Leu Asn
                405                 410

<210> SEQ ID NO 9
<211> LENGTH: 390
<212> TYPE: PRT
<213> ORGANISM: Chlamydia trachomatis

<400> SEQUENCE: 9

Ser Leu Thr Val Pro Val Ser Ala Tyr Leu Gly Phe Asp Pro Thr Ala
1               5                   10                  15

Pro Ser Leu His Ile Gly His Trp Ile Gly Ile Cys Phe Leu Arg Arg
            20                  25                  30

Leu Ala Ala Tyr Gly Ile Thr Pro Val Ala Leu Val Gly Gly Ala Thr
        35                  40                  45

Gly Met Ile Gly Asp Pro Ser Gly Lys Ser Val Glu Arg Ser Leu Leu
    50                  55                  60

Asp Gln Ala Gln Val Leu Asp Asn Ser Lys Lys Ile Ala Ala Ala Leu
65                  70                  75                  80

Ala Ser Tyr Leu Pro Gly Ile Arg Ile Val Asn Asn Ala Asp Trp Leu
                85                  90                  95

Gly Ser Leu Ser Met Val Asp Phe Leu Arg Asp Val Gly Lys His Phe
            100                 105                 110

Arg Leu Gly Ser Met Leu Ala Lys Asp Val Val Lys Gln Arg Val Tyr
        115                 120                 125

Ser Glu Glu Gly Ile Ser Tyr Thr Glu Phe Ser Tyr Leu Leu Leu Gln
    130                 135                 140

Ser Tyr Asp Phe Ala His Leu Phe Lys Glu His Asn Val Val Leu Gln
145                 150                 155                 160

Cys Gly Gly Ser Asp Gln Trp Gly Asn Ile Thr Ser Gly Ile Asp Tyr
                165                 170                 175

Ile Arg Arg Arg Gly Leu Gly Gln Ala Tyr Gly Leu Thr Tyr Pro Leu
            180                 185                 190

Leu Thr Asp Ser Lys Gly Lys Lys Ile Gly Lys Thr Glu Ser Gly Thr
        195                 200                 205

Ile Trp Leu Asp Pro Ala Leu Thr Pro Pro Tyr Glu Leu Phe Gln Tyr
    210                 215                 220

Phe Leu Arg Leu Pro Asp Gln Glu Ile Ser Lys Val Met Arg Thr Leu
225                 230                 235                 240

Thr Leu Leu Asp Asn Glu Glu Ile Phe Ala Leu Asp Glu Arg Leu Thr
                245                 250                 255

Ser Asp Pro Gln Ala Val Lys Lys Tyr Ile Ala Glu Val Ile Val Lys
            260                 265                 270

Asp Val His Gly Ser Glu Gly Leu Ala Gln Ala Gln Ala Ala Thr Glu
        275                 280                 285

Ser Phe Phe Ala Ser Lys Gly Lys Ser Ile Thr Glu Ala Glu Leu Val
```

```
                   290                 295                 300

Ala Leu Val Glu Ser Gly Val Gly Val Lys Val Ala Arg Ala Asp Leu
305                 310                 315                 320

Ile Gly Lys Arg Trp Leu Asp Ile Val Glu Leu Gly Phe Cys Ser
                325                 330                 335

Ser Arg Gly Gln Ala Arg Arg Leu Ile Gln Gln Arg Gly Leu Tyr Ile
                340                 345                 350

Asn Gln Glu Pro Leu Ala Asp Glu Gln Ser Ile Leu Asp Gly Thr Gln
                355                 360                 365

Leu Cys Phe Asp Arg Tyr Val Leu Leu Ser Gln Gly Lys Arg Lys Lys
370                 375                 380

Gln Val Ile Asp Leu Asn
385                 390

<210> SEQ ID NO 10
<211> LENGTH: 298
<212> TYPE: PRT
<213> ORGANISM: Chlamydia trachomatis

<400> SEQUENCE: 10

Met Leu Lys Ile Asp Leu Thr Gly Lys Ile Ala Phe Ile Ala Gly Ile
1               5                   10                  15

Gly Asp Asp Asn Gly Tyr Gly Trp Gly Ile Ala Lys Met Leu Ala Glu
                20                  25                  30

Ala Gly Ala Thr Ile Leu Val Gly Thr Trp Val Pro Ile Tyr Lys Ile
                35                  40                  45

Phe Ser Gln Ser Leu Glu Leu Gly Lys Phe Asn Ala Ser Arg Glu Leu
50                  55                  60

Ser Asn Gly Glu Leu Leu Thr Phe Ala Lys Ile Tyr Pro Met Asp Ala
65                  70                  75                  80

Ser Phe Asp Thr Pro Glu Asp Ile Pro Gln Glu Ile Leu Glu Asn Lys
                85                  90                  95

Arg Tyr Lys Asp Leu Ser Gly Tyr Thr Val Ser Glu Val Glu Gln
                100                 105                 110

Val Lys Lys His Phe Gly His Ile Asp Ile Leu Val His Ser Leu Ala
                115                 120                 125

Asn Ser Pro Glu Ile Ala Lys Pro Leu Leu Asp Thr Ser Arg Lys Gly
130                 135                 140

Tyr Leu Ala Ala Leu Ser Thr Ser Ser Tyr Ser Phe Ile Ser Leu Leu
145                 150                 155                 160

Ser His Phe Gly Pro Ile Met Asn Ala Gly Ala Ser Thr Ile Ser Leu
                165                 170                 175

Thr Tyr Leu Ala Ser Met Arg Ala Val Pro Gly Tyr Gly Gly Gly Met
                180                 185                 190

Asn Ala Ala Lys Ala Ala Leu Glu Ser Asp Thr Lys Val Leu Ala Trp
                195                 200                 205

Glu Ala Gly Arg Arg Trp Gly Val Arg Val Asn Thr Ile Ser Ala Gly
210                 215                 220

Pro Leu Ala Ser Arg Ala Gly Lys Ala Ile Gly Phe Ile Glu Arg Met
225                 230                 235                 240

Val Asp Tyr Tyr Gln Asp Trp Ala Pro Leu Pro Ser Pro Met Glu Ala
                245                 250                 255

Glu Gln Val Gly Ala Ala Ala Phe Leu Val Ser Pro Leu Ala Ser
                260                 265                 270

Ala Ile Thr Gly Glu Thr Leu Tyr Val Asp His Gly Ala Asn Val Met
```

```
                         275                 280                 285

Gly Ile Gly Pro Glu Met Phe Pro Lys Asp
        290                 295

<210> SEQ ID NO 11
<211> LENGTH: 102
<212> TYPE: PRT
<213> ORGANISM: Chlamydia trachomatis

<400> SEQUENCE: 11

Met Ser Asp Gln Ala Thr Thr Leu Lys Ile Lys Pro Leu Gly Asp Arg
1               5                   10                  15

Ile Leu Val Lys Arg Glu Glu Glu Ala Ser Thr Ala Arg Gly Gly Ile
            20                  25                  30

Ile Leu Pro Asp Thr Ala Lys Lys Lys Gln Asp Arg Ala Glu Val Leu
        35                  40                  45

Ala Leu Gly Thr Gly Lys Lys Asp Asp Lys Gly Gln Gln Leu Pro Phe
    50                  55                  60

Glu Val Gln Val Gly Asn Ile Val Leu Ile Asp Lys Tyr Ser Gly Gln
65                  70                  75                  80

Glu Leu Thr Val Glu Gly Glu Tyr Val Ile Val Gln Met Ser Glu
                85                  90                  95

Val Ile Ala Val Leu Gln
            100

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gly Tyr Lys Asp Gly Asn Glu Tyr Ile
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct

<400> SEQUENCE: 13

Ser Ile Ile Asn Phe Glu Lys Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct

<400> SEQUENCE: 14

Arg Pro Gln Ala Ser Gly Val Tyr Met
1               5
```

US 8,637,053 B2

CHLAMYDIA ANTIGENS

CROSS-REFERENCE TO RELATED APPLICATIONS

This application is the U.S. National Stage of International Application No. PCT/US2008/13298, filed Dec. 3, 2008, which, in turn, claims the benefit of U.S. Provisional Application No. 61/005,209, filed Dec. 3, 2007.

BACKGROUND OF THE INVENTION

*Chlamydia trachomatis* is an intracellular bacterial pathogen that colonizes and infects oculogenital surfaces. Ocular infections of *Chlamydia trachomatis* cause trachoma, a chronic follicular conjunctivitis that results in scarring and blindness. The World Health Organization (WHO) estimates that 300-500 million people worldwide are afflicted by trachoma (Resnikoff et al., *Bull. WHO* 82:844-851, 2004), making it the most prevalent form of infectious preventable blindness (Whitcher et al. *Bull. WHO* 79:214-221, 2001). Urogenital infections are the leading cause of bacterial sexually transmitted diseases (Division of STD Prevention, Sexually Transmitted Disease Surveillance 1997, Centers Dis. Cont. Prev., Atlanta, 1998) in both developing and industrialized nations (WHO, Global Prevalence and Incidence of Selected Curable Sexually Transmitted Infections: Overview and Estimates, WHO, Geneva, 2001). Moreover, sexually transmitted diseases are risk factors for the transmission of HIV (Plummer et al., *J. Infect. Dis.* 163:233-239, 1991), infertility (Westrom et al., *Sex. Trans. Dis.* 19:185-192, 1991), and human papilloma virus-induced cervical neoplasia (Anttila et al., *J. Am. Med. Assoc.* 285:47-51, 2001).

For all the above reasons, control of *C. trachomatis* infections is an important public health goal.

SUMMARY OF THE INVENTION

The present invention features *C. trachomatis* antigens, and the therapeutic uses of such antigens. The antigens of the present invention may be used to treat or prevent *Chlamydia* infection in a subject.

In a first aspect, the present invention provides an isolated CT491 polypeptide containing a sequence substantially identical SEQ ID NO: 1, or fragment thereof, which elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional aspect of the invention is an isolated fragment of a CT491 polypeptide, which is fewer than 464, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length and elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay. Desirable CT491 fragments have at least 7 amino acids and/or elicit a CD8⁺ T cell response.

A related embodiment of the invention provides an isolated fragment of a CT491 polypeptide, which is (1) fewer than 464, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 1; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional embodiment of the invention provides an isolated fragment of a CT491 polypeptide, which is (1) fewer than 464, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 1 and/or has at least one flanking amino acid (e.g., 1, 2, 3, 4, 5, 6, 7, 8, 9, or 10 flanking amino acids) at the N- and/or C-terminus of the sequence of SEQ ID NO: 1; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

A second aspect of the present invention is an isolated CT601 polypeptide containing a sequence substantially identical SEQ ID NO: 2, or fragment thereof, which elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional aspect of the invention is an isolated fragment of a CT601 polypeptide, which is fewer than 200, 190, 180, 170, 160, 150, 140, 130, 120, 110, 100, 90, 80, 70, 60, 50, 40, 35, 30, 25, 20, or 15 amino acids in length and elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay. Desirable CT601 fragments have at least 7 amino acids and/or elicit a CD8⁺ T cell response.

A related embodiment of the invention provides an isolated fragment of a CT601 polypeptide, which is (1) fewer than 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 2; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional embodiment of the invention provides an isolated fragment of a CT601 polypeptide, which is (1) fewer than 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 2 and/or has at least one flanking amino acid (e.g., 1, 2, 3, 4, 5, 6, 7, 8, 9, or 10 flanking amino acids) at the N- and/or C-terminus of the sequence of SEQ ID NO: 2; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

In a third aspect, the present invention provides an isolated CT687 polypeptide containing a sequence substantially identical SEQ ID NO: 3, or fragment thereof, which elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional aspect of the invention is an isolated fragment of a CT687 polypeptide, which is fewer than 401, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length and elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay. Desirable CT687 fragments have at least 7 amino acids and/or elicit a CD8⁺ T cell response.

A related embodiment of the invention provides an isolated fragment of a CT687 polypeptide, which is (1) fewer than 401, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 3; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional embodiment of the invention provides an isolated fragment of a CT687 polypeptide, which is (1) fewer than 401, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 3 and/or has at least one flanking amino acid (e.g., 1, 2, 3, 4, 5, 6, 7, 8, 9, or 10 flanking amino acids) at the N- and/or C-terminus of the sequence of SEQ ID NO: 3; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

In a fourth aspect, the present invention provides an isolated CT732 polypeptide containing a sequence substantially identical SEQ ID NO: 4, or fragment thereof, which elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional aspect of the invention is an isolated fragment of a CT732 polypeptide, which is fewer than 157, 150, 140, 130, 120, 110, 100, 90, 80, 70, 60, 50, 40, 35, 30, 25, 20, or 15 amino acids in length and elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay. Desirable CT732 fragments have at least 7 amino acids and/or elicit a CD8⁺ T cell response.

A related embodiment of the invention provides an isolated fragment of a CT732 polypeptide, which is (1) fewer than 157, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 4; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional embodiment of the invention provides an isolated fragment of a CT732 polypeptide, which is (1) fewer than 157, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 4 and/or has at least one flanking amino acid (e.g., 1, 2, 3, 4, 5, 6, 7, 8, 9, or 10 flanking amino acids) at the N- and/or C-terminus of the sequence of SEQ ID NO: 4; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

In a fifth aspect, the present invention provides an isolated CT781 polypeptide containing a sequence substantially identical SEQ ID NO: 5, or fragment thereof, which elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional aspect of the invention is an isolated fragment of a CT781 polypeptide, which is fewer than 526, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length and elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay. Desirable CT781 fragments have at least 7 amino acids and/or elicit a CD8⁺ T cell response.

A related embodiment of the invention provides an isolated fragment of a CT781 polypeptide, which is (1) fewer than 526, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 5; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional embodiment of the invention provides an isolated fragment of a CT781 polypeptide, which is (1) fewer than 526, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 5 and/or has at least one flanking amino acid (e.g., 1, 2, 3, 4, 5, 6, 7, 8, 9, or 10 flanking amino acids) at the N- and/or C-terminus of the sequence of SEQ ID NO: 5; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

In a sixth aspect, the present invention provides an isolated CT808 polypeptide containing a sequence substantially identical SEQ ID NO: 6, or fragment thereof, which elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional aspect of the invention is an isolated fragment of a CT808 polypeptide, which is fewer than 512, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length and elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay. Desirable CT808 fragments have at least 7 amino acids and/or elicit a CD8+ T cell response.

A related embodiment of the invention provides an isolated fragment of a CT808 polypeptide, which is (1) fewer than 512, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 6; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional embodiment of the invention provides an isolated fragment of a CT808 polypeptide, which is (1) fewer than 512, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 6 and/or has at least one flanking amino acid (e.g., 1, 2, 3, 4, 5, 6, 7, 8, 9, or 10 flanking amino acids) at the N- and/or C-terminus of the sequence of SEQ ID NO: 6; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

In a seventh aspect, the present invention provides an isolated CT823 polypeptide containing a sequence substantially identical SEQ ID NO: 7, or fragment thereof, which elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional aspect of the invention is an isolated fragment of a CT823 polypeptide, which is fewer than 497, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length and elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay. Desirable CT823 fragments have at least 7 amino acids and/or elicit a CD8+ T cell response.

A related embodiment of the invention provides an isolated fragment of a CT823 polypeptide, which is (1) fewer than 497, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 7; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional embodiment of the invention provides an isolated fragment of a CT823 polypeptide, which is (1) fewer than 497, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 7 and/or has at least one flanking amino acid (e.g., 1, 2, 3, 4, 5, 6, 7, 8, 9, or 10 flanking amino acids) at the N- and/or C-terminus of the sequence of SEQ ID NO: 7; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

In an eighth aspect, the present invention provides an isolated CT062 polypeptide containing a sequence substantially identical SEQ ID NO: 8, which elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

A related embodiment of the invention provides a CT062 polypeptide, which (1) contains at least one, preferably at least 2, 3, 4, 5, 6, 7, 8, 9, or 10 conservative amino acid substitutions in the sequence of SEQ ID NO: 8 and/or has at least one flanking amino acid (e.g., 1, 2, 3, 4, 5, 6, 7, 8, 9, or 10 flanking amino acids) at the N- and/or C-terminus of the sequence of SEQ ID NO: 8; and (2) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

In an ninth aspect, the present invention provides an isolated CT062 fragment containing a sequence substantially identical SEQ ID NO: 9 (i.e., amino acids 23-412 of full-length CT062), which elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional aspect of the invention is an isolated fragment of a CT062 polypeptide, which is fewer than 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length and elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay. Desirable CT062 fragments have at least 7 amino acids and/or elicit a CD8+ T cell response.

A related embodiment of the invention provides an isolated fragment of a CT062 polypeptide, which is (1) fewer than 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or amino acids in length; (2) contains at least one, preferably at least 2, 3, 4, 5, 6, 7, 8, 9, or 10 conservative amino acid substitutions in the sequence of SEQ ID NO: 9 and/or has at least one flanking amino acid (e.g., 1, 2, 3, 4, 5, 6, 7, 8, 9, or 10 flanking amino acids) at the N- and/or C-terminus of the sequence of SEQ ID NO: 9; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

In a tenth aspect, the present invention provides an isolated CT104 polypeptide containing a sequence substantially identical SEQ ID NO: 10, or fragment thereof, which elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional aspect of the invention is an isolated fragment of a CT104 polypeptide, which is fewer than 298, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length and elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay. Desirable CT104 fragments have at least 7 amino acids and/or elicit a CD8+ T cell response.

A related embodiment of the invention provides an isolated fragment of a CT104 polypeptide, which is (1) fewer than 298, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 10; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional embodiment of the invention provides an isolated fragment of a CT104 polypeptide, which is (1) fewer than 298, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 10 and/or has at least one flanking amino acid (e.g., 1, 2, 3, 4, 5, 6, 7, 8, 9, or 10 flanking amino acids) at the N- and/or C-terminus of the sequence of SEQ ID NO: 10; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

In an eleventh aspect, the present invention provides an isolated CT111 polypeptide containing a sequence substantially identical SEQ ID NO: 11, or fragment thereof, which elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional aspect of the invention is an isolated fragment of a CT111 polypeptide, which is fewer than 102, 100, 90, 80, 70, 60, 50, 40, 35, 30, 25, 20, or 15 amino acids in length and elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay. Desirable CT111 fragments have at least 7 amino acids and/or elicit a CD8+ T cell response.

A related embodiment of the invention provides an isolated fragment of a CT111 polypeptide, which is (1) fewer than 102, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 11; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

An additional embodiment of the invention provides an isolated fragment of a CT111 polypeptide, which is (1) fewer than 102, 100, 90, 80, 70, 60, 50, 40, 35, 30, 25, 20, or 15 amino acids in length; (2) contains at least one, preferably at least 2, 3, 4, 5, 6, 7, 8, 9, or 10 conservative amino acid substitutions in the sequence of SEQ ID NO: 11 and/or has at least one flanking amino acid (e.g., 1, 2, 3, 4, 5, 6, 7, 8, 9, or 10 flanking amino acids) at the N- and/or C-terminus of the sequence of SEQ ID NO: 11; and (3) elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production elicited from a non-immunogenic peptide in the same assay.

The invention further provides a fusion protein containing (1) the sequence of any of the above polypeptides or fragments of the invention, and (2) a fusion partner.

The invention further provides pharmaceutical compositions containing one or more (e.g., 1, 2, 3, 4, 5, 6, 7, 8, 9, or 10) of any of the above described polypeptides, fragments, and fusion proteins of the invention and a pharmaceutically acceptable carrier.

The invention additionally provides vaccines containing one or more (e.g., 1, 2, 3, 4, 5, 6, 7, 8, 9, or 10) of any of the above described polypeptides, fragments, and fusion proteins of the invention and a pharmaceutically acceptable carrier. Additionally, the invention provides DNA vaccines containing a polynucleotide sequence that encodes one or more (e.g., 1, 2, 3, 4, 5, 6, 7, 8, 9, or 10) of any of the above described polypeptides, fragments, and fusion proteins of the invention and a pharmaceutically acceptable carrier.

In preferred embodiments of all the above aspects, the polypeptides, polypeptide fragments, fusion proteins, and vaccines of the invention (e.g., protein and DNA vaccines) elicit an immune response when administered to a mammal. Desirably, the polypeptides, polypeptide fragments, fusion proteins, and vaccines of the invention elicit an immune response when administered to a human.

The invention further provides a method of treating or preventing a bacterial infection, preferably a *Chlamydia* infection, by administering to a subject in need thereof (e.g., a subject who has or is at risk for contracting *Chlamydia*), a therapeutically effective amount of one or more (e.g., 1, 2, 3, 4, 5, 6, 7, 8, 9, or 10) of any of the above described polypeptides, fragments, fusion proteins, vaccines (e.g., protein vaccines or DNA vaccines) of the present invention. In a desirable embodiments of the method of the invention, the polypeptide, fragment, fusion protein, or vaccine (e.g., protein vaccines or DNA vaccines) of the present invention is capable of reducing (e.g., at least a 10%, 20%, 30%, 40%, 50%, 60%, 70%, 80%, 90%, or even 100% reduction) one or more symptoms of *C. trachomatis* infection in a patient (e.g., cystitis, pain during urination, pain or bleeding during or after sexual intercourse, abdominal pains, irregular menstrual bleeding, painful swelling and irritation of the eyes, white/cloudy and watery penile discharge, fever, lower back pain, and swollen or painful testicles) or reducing the likelihood (e.g., at least a 5%, 10%, 20%, 30%, 40%, 50%, 60%, 70%, 80%, 90%, or even 100% reduction) of becoming infected with *C. trachomatis*.

In desirable embodiments of the method, the polypeptide, fragment, fusion protein, or vaccine (e.g., protein vaccines or DNA vaccines) of the present invention is capable of generating an immune response in a subject and/or is administered in a pharmaceutically acceptable carrier.

DEFINITIONS

By a "CT491 polypeptide" is meant a polypeptide that is substantially identical to the amino acid sequence of SEQ ID NO: 1. Desirably, a CT491 polypeptide has at least 80%, 85%, 90%, 95%, 99%, or even 100% sequence identity to the amino acid sequence of SEQ ID NO: 1. Desirably, a CT491 polypeptide elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay).

By a "fragment of a CT491 polypeptide" or a "CT491 fragment" is meant a fragment of a CT491 polypeptide that contains fewer than 464 amino acids. Desirably, a CT491 fragment elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay). Desirably, the fragment contains fewer than 464, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 35, 30, 25, 20, 15, or 10 amino acids, and desirably, is immunogenic. Preferred CT491 fragments are between 7 and 463 amino acids in length (e.g., 7, 8, 9, 10, 11, 12, 13, 14, 15, 16, 17, 18, 19, 20, 40, 50, 100, or 150 amino acids in length). A CT491 fragment may contain one or more conservative amino acid substitutions in the sequence of SEQ ID NO: 1. Additional desirable CT491 fragments contain one or more conservative amino acid substitutions in the sequence of SEQ ID NO: 1 and/or have at least one flanking amino acid (e.g., 1, 2, 3, 4, 5, 6, 7, 8, 9, 10, 11, 12, 13, 14, or 15 flanking amino acids) at the N- and/or C-terminus of the sequence of SEQ ID NO: 1. Other preferred CT491 fragments contain seven or more continuous amino acids of the sequence of SEQ ID NO: 1.

Non-limiting examples of a CT491 fragment include amino acids 1-40, 10-50, 20-60, 30-70, 40-80, 50-90, 60-100, 70-110, 80-120, 90-130, 100-140, 110-150, 120-160, 130-170, 140-180, 150-190, 160-200, 170-210, 180-220, 190-230, 200-240, 210-250, 220-260, 230-270, 240-280, 250-290, 260-300, 270-310, 280-320, 290-330, 300-340, 310-350, 320-360, 330-370, 340-380, 350-390, 360-400, 370-410, 380-420, 390-430, 400-440, 410-450, 420-460, and 424-464 of the sequence of SEQ ID NO: 1; and these fragments having one or more of the following features: one or more conservative amino acid substitutions (e.g., 1, 2, 3, 4, 5, 6, 7, 8, 9, 10, 11, 12, 13, 14, 15, or 16 conservative amino acid substitutions) in the sequence of SEQ ID NO: 1; one or more amino acids (e.g., 1, 2, 3, 4, 5, 6, 7, 8, 9, 10, 11, 12, 13, 14, 15, or 16 amino acids) truncated from the N and/or C-terminus of the sequence of SEQ ID NO: 1; and at least one flanking amino acid (e.g., 1, 2, 3, 4, 5, 6, 7, 8, 9, 10, 11, 12, 13, 14, or 15 flanking amino acids) at the N- and/or C-terminus of the sequence of SEQ ID NO: 1.

By a "CT601 polypeptide" is meant a polypeptide that is substantially identical to the amino acid sequence of SEQ ID NO: 2. Desirably, a CT601 polypeptide has at least 80%, 85%, 90%, 95%, 99%, or even 100% sequence identity to the amino acid sequence of SEQ ID NO: 2. Desirably, a CT601 polypeptide elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay).

By a "fragment of a CT601 polypeptide" or "CT601 fragment" is meant a fragment of a CT601 polypeptide containing fewer than 200 amino acids. Desirably, a CT601 fragment elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay). Desirably, the fragment is fewer than 200, 190, 180, 170, 160, 150, 140, 130, 120, 110, 100, 90, 80, 70, 60, 50, 40, 30, 25, 20, 15, or 10 amino acids in length, and desirably, is immunogenic. Preferred CT601 fragments are between 7 and 199 amino acids in length (e.g., 7, 8, 9, 10, 11, 12, 13, 14, 15, 16, 17, 18, 19, 20, 40, 50, 100, or 150 amino acids in length). A CT601 fragment may contain one or more conservative amino acid substitutions in the sequence of SEQ ID NO: 2. Additional desirable CT601 fragments contain one or more conservative amino acid substitutions in the sequence of SEQ ID NO: 2 and/or at least one flanking amino acid (e.g., 1, 2, 3, 4, 5, 6, 7, 8, 9, or 10 flanking amino acids) at the N- and/or C-terminus of the sequence of SEQ ID NO: 2. Other preferred CT601 fragments contain seven or more continuous amino acids of the sequence of SEQ ID NO: 2.

Non-limiting examples of a CT601 fragment include amino acids 1-40, 10-50, 20-60, 30-70, 40-80, 50-90, 60-100, 70-110, 80-120, 90-130, 100-140, 110-150, 120-160, 130-170, 140-180, 150-190, and 160-200 of the sequence of SEQ ID NO: 2; and these fragments having one or more of the following features: one or more conservative amino acid substitutions (e.g., 1, 2, 3, 4, 5, 6, 7, 8, 9, 10, 11, 12, 13, 14, 15, or 16 conservative amino acid substitutions) in the sequence of SEQ ID NO: 2; one or more amino acids (e.g., 1, 2, 3, 4, 5, 6, 7, 8, 9, 10, 11, 12, 13, 14, 15, or 16 amino acids) truncated from the N and/or C-terminus of the sequence of SEQ ID NO: 2; and at least one flanking amino acid (e.g., 1, 2, 3, 4, 5, 6, 7, 8, 9, or 10 flanking amino acids) at the N- and/or C-terminus of the sequence of SEQ ID NO: 2.

By a "CT687 polypeptide" is meant a polypeptide that is substantially identical to the amino acid sequence of SEQ ID NO: 3. Desirably, a CT687 polypeptide has at least 80%, 85%, 90%, 95%, 99%, or even 100% identity to the amino acid sequence of SEQ ID NO: 3. Desirably, a CT687 polypeptide elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay).

By "fragment of a CT687 polypeptide" or a "CT687 fragment" is meant a fragment of a CT687 polypeptide containing fewer than 401 amino acids. Preferred CT687 fragments are between 7 and 400 amino acids in length (e.g., 7, 8, 9, 10, 11, 12, 13, 14, 15, 16, 17, 18, 19, 20, 40, 50, 100, or 150 amino acids in length). Desirably, a CT687 fragment elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay). Desirably, the fragment is fewer than 401, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 25, 20, 15, or 10 amino acids, and desirably, is immunogenic. A CT687 fragment may contain one or more conservative amino acid substitutions in the sequence of SEQ ID NO: 3. Additional desirable CT687 fragments contain one or more conservative amino acid substitutions in the sequence of SEQ ID NO: 3 and/or at least one flanking amino acid (e.g., 1, 2, 3, 4, 5, 6, 7, 8, 9, or 10 flanking amino acids) at the N- and/or C-terminus of the sequence of SEQ ID NO: 3. Other preferred CT687 fragments contain seven or more continuous amino acids of the sequence of SEQ ID NO: 3.

Non-limiting examples of a CT687 fragment include amino acids 1-40, 10-50, 20-60, 30-70, 40-80, 50-90, 60-100, 70-110, 80-120, 90-130, 100-140, 110-150, 120-160, 130-170, 140-180, 150-190, 160-200, 170-210, 180-220, 190-230, 200-240, 210-250, 220-260, 230-270, 240-280, 250-290, 260-300, 270-310, 280-320, 290-330, 300-340, 310-350, 320-360, 330-370, 340-380, 350-390, and 360-401 of the sequence of SEQ ID NO: 3; and these fragments having one or more of the following features: one or more conservative amino acid substitutions (e.g., 1, 2, 3, 4, 5, 6, 7, 8, 9, 10, 11, 12, 13, 14, 15, or 16 conservative amino acid substitutions) in the sequence of SEQ ID NO: 3; one or more amino acids (e.g., 1, 2, 3, 4, 5, 6, 7, 8, 9, 10, 11, 12, 13, 14, 15, or 16 amino acids) truncated from the N- and/or C-terminus of the sequence of SEQ ID NO: 3; and at least one flanking amino acid (e.g., 1, 2, 3, 4, 5, 6, 7, 8, 9, or flanking amino acids) at the N- and/or C-terminus of the sequence of SEQ ID NO: 3.

By a "CT732 polypeptide" is meant a polypeptide that is substantially identical to the amino acid sequence of SEQ ID NO: 4. Desirably, a CT732 polypeptide has at least 80%, 85%, 90%, 95%, 99%, or even 100% identity to the amino acid sequence of SEQ ID NO: 4. Desirably, a CT732 polypeptide elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay).

By "fragment of a CT732 polypeptide" or a "CT732 fragment" is meant a fragment of a CT732 polypeptide containing fewer than 157 amino acids. Preferred CT732 fragments are between 7 and 156 amino acids in length (e.g., 7, 8, 9, 10, 11, 12, 13, 14, 15, 16, 17, 18, 19, 20, 40, 50, 100, or 150 amino acids in length). Desirably, a CT732 fragment elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay). Desirably, the fragment is fewer than 157, 150, 140, 130, 120, 110, 100, 90, 80, 70, 60, 50, 40, 30, 25, 20, 15, or amino acids, and desirably, is immunogenic. A CT732 fragment may contain one or more conservative amino acid substitutions in the sequence of SEQ ID NO: 4. Additional desirable CT732 fragments contain one or more conservative amino acid substitutions in the sequence of SEQ ID NO: 4 and/or at least one flanking amino acid (e.g., 1, 2, 3, 4, 5, 6, 7, 8, 9, or 10 flanking amino acids) at the N- and/or C-terminus of the sequence of SEQ ID NO: 4. Other preferred CT732 fragments contain seven or more continuous amino acids of the sequence of SEQ ID NO: 4.

Non-limiting examples of a CT732 fragment include amino acids 1-40, 10-50, 20-60, 30-70, 40-80, 50-90, 60-100, 70-110, 80-120, 90-130, 100-140, 110-150, and 120-157 of the sequence of SEQ ID NO: 4; and these fragments having one or more of the following features: one or more conservative amino acid substitutions (e.g., 1, 2, 3, 4, 5, 6, 7, 8, 9, 10, 11, 12, 13, 14, 15, or 16 conservative amino acid substitutions) in the sequence of SEQ ID NO: 4; one or more amino acids (e.g., 1, 2, 3, 4, 5, 6, 7, 8, 9, 10, 11, 12, 13, 14, 15, or 16 amino acids) truncated from the N and/or C-terminus of the sequence of SEQ ID NO: 4; and at least one flanking amino acid (e.g., 1, 2, 3, 4, 5, 6, 7, 8, 9, or flanking amino acids) at the N- and/or C-terminus of the sequence of SEQ ID NO: 4.

By a "CT781 polypeptide" is meant a polypeptide that is substantially identical to the amino acid sequence of SEQ ID NO: 5. Desirably, a CT781 polypeptide has at least 80%, 85%, 90%, 95%, 99%, or even 100% identity to the amino acid sequence of SEQ ID NO: 5. Desirably, a CT781 polypeptide elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay).

By "fragment of a CT781 polypeptide" or a "CT781 fragment" is meant a fragment of a CT781 polypeptide containing fewer than 526 amino acids. Preferred CT781 fragments are between 7 and 525 amino acids in length (e.g., 7, 8, 9, 10, 11, 12, 13, 14, 15, 16, 17, 18, 19, 20, 40, 50, 100, or 150 amino acids in length). Desirably, a CT781 fragment elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay). Desirably, the fragment is fewer than 526, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 25, 20, 15, or 10 amino acids, and desirably, is immunogenic. A CT781 fragment may contain one or more conservative amino acid substitutions in the sequence of SEQ ID NO: 5. Additional desirable CT781 fragments contain one or more conservative amino acid substitutions in the sequence of SEQ ID NO: 5 and/or at least one flanking amino acid (e.g., 1, 2, 3, 4, 5, 6, 7, 8, 9, or 10 flanking amino acids) at the N- and/or C-terminus of the sequence of SEQ ID NO: 5. Other preferred CT781 fragments contain seven or more continuous amino acids of the sequence of SEQ ID NO: 5.

Non-limiting examples of a CT781 fragment include amino acids 1-40, 10-50, 20-60, 30-70, 40-80, 50-90, 60-100, 70-110, 80-120, 90-130, 100-140, 110-150, 120-160, 130-170, 140-180, 150-190, 160-200, 170-210, 180-220, 190-230, 200-240, 210-250, 220-260, 230-270, 240-280, 250-290, 260-300, 270-310, 280-320, 290-330, 300-340, 310-350, 320-360, 330-370, 340-380, 350-390, 360-400, 370-410, 380-420, 390-430, 400-440, 410-450, 420-460, 430-470, 440-480, 450-490, 460-500, 470-510, 480-520, and 485-526 of the sequence of SEQ ID NO: 5; and these fragments having one or more of the following features: one or more conservative amino acid substitutions (e.g., 1, 2, 3, 4, 5, 6, 7, 8, 9, 10, 11, 12, 13, 14, 15, or 16 conservative amino acid substitutions) in the sequence of SEQ ID NO: 5; one or more amino acids (e.g., 1, 2, 3, 4, 5, 6, 7, 8, 9, 10, 11, 12, 13, 14, 15, or 16 amino acids) truncated from the N and/or C-terminus of the sequence of SEQ ID NO: 5; and at least one flanking amino acid (e.g., 1, 2, 3, 4, 5, 6, 7, 8, 9, or 10 flanking amino acids) at the N- and/or C-terminus of the sequence of SEQ ID NO: 5.

By a "CT808 polypeptide" is meant a polypeptide that is substantially identical to the amino acid sequence of SEQ ID NO: 6. Desirably, a CT808 polypeptide has at least 80%, 85%, 90%, 95%, 99%, or even 100% identity to the amino acid sequence of SEQ ID NO: 6. Desirably, a CT808 polypeptide elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay).

By "fragment of a CT808 polypeptide" or a "CT808 fragment" is meant a fragment of a CT808 polypeptide containing fewer than 512 amino acids. Preferred CT808 fragments are between 7 and 511 amino acids in length (e.g., 7, 8, 9, 10, 11, 12, 13, 14, 15, 16, 17, 18, 19, 20, 40, 50, 100, or 150 amino acids in length). Desirably, a CT808 fragment elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay). Desirably, the fragment is fewer than 512, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 25, 20, 15, or 10 amino acids, and desirably, is immunogenic. A CT808 fragment may contain one or more conservative amino acid substitutions in the sequence of SEQ ID NO: 6. Additional desirable CT808 fragments contain one or more conservative amino acid substitutions in the sequence of SEQ ID NO: 6 and/or at least one flanking amino acid (e.g., 1, 2, 3, 4, 5, 6, 7, 8, 9, or 10 flanking amino acids) at the N- and/or C-terminus of the sequence of SEQ ID NO: 6. Other preferred CT808 fragments contain seven or more continuous amino acids of the sequence of SEQ ID NO: 6.

Non-limiting examples of a CT808 fragment include amino acids 1-40, 10-50, 20-60, 30-70, 40-80, 50-90, 60-100, 70-110, 80-120, 90-130, 100-140, 110-150, 120-160, 130-170, 140-180, 150-190, 160-200, 170-210, 180-220, 190-230, 200-240, 210-250, 220-260, 230-270, 240-280, 250-290, 260-300, 270-310, 280-320, 290-330, 300-340, 310-350, 320-360, 330-370, 340-380, 350-390, 360-400, 370-410, 380-420, 390-430, 400-440, 410-450, 420-460, 430-470, 440-480, 450-490, 460-500, and 470-512 of the sequence of SEQ ID NO: 6; and these fragments having one or more of the following features: one or more conservative amino acid substitutions (e.g., 1, 2, 3, 4, 5, 6, 7, 8, 9, 10, 11, 12, 13, 14, 15, or 16 conservative amino acid substitutions) in the sequence of SEQ ID NO: 6; one or more amino acids (e.g., 1, 2, 3, 4, 5, 6, 7, 8, 9, 10, 11, 12, 13, 14, 15, or 16 amino acids) truncated from the N and/or C-terminus of the sequence of SEQ ID NO: 6; and at least one flanking amino acid (e.g., 1, 2, 3, 4, 5, 6, 7, 8, 9, or 10 flanking amino acids) at the N- and/or C-terminus of the sequence of SEQ ID NO: 6.

By a "CT823 polypeptide" is meant a polypeptide that is substantially identical to the amino acid sequence of SEQ ID NO: 7. Desirably, a CT823 polypeptide has at least 80%, 85%, 90%, 95%, 99%, or even 100% identity to the amino acid sequence of SEQ ID NO: 7. Desirably, a CT823 polypeptide elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay).

By "fragment of a CT823 polypeptide" or a "CT823 fragment" is meant a fragment of a CT823 polypeptide containing fewer than 497 amino acids. Preferred CT823 fragments are between 7 and 496 amino acids in length (e.g., 7, 8, 9, 10, 11, 12, 13, 14, 15, 16, 17, 18, 19, 20, 40, 50, 100, or 150 amino acids in length). Desirably, a CT823 fragment elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay). Desirably, the fragment is fewer than 497, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 25, 20, 15, or 10 amino acids, and desirably, is immunogenic. A CT823 fragment may contain one or more conservative amino acid substitutions in the sequence of SEQ ID NO: 7. Additional desirable CT823 fragments contain one or more conservative amino acid substitutions in the sequence of SEQ ID NO: 7 and/or at least one flanking amino acid (e.g., 1, 2, 3, 4, 5, 6, 7, 8, 9, or 10 flanking amino acids) at the N- and/or C-terminus of the sequence of SEQ ID NO: 7. Other preferred CT823 fragments contain seven or more continuous amino acids of the sequence of SEQ ID NO: 7.

Non-limiting examples of a CT823 fragment include amino acids 1-40, 10-50, 20-60, 30-70, 40-80, 50-90, 60-100, 70-110, 80-120, 90-130, 100-140, 110-150, 120-160, 130-170, 140-180, 150-190, 160-200, 170-210, 180-220, 190-230, 200-240, 210-250, 220-260, 230-270, 240-280, 250-290, 260-300, 270-310, 280-320, 290-330, 300-340, 310-350, 320-360, 330-370, 340-380, 350-390, 360-400, 370-410, 380-420, 390-430, 400-440, 410-450, 420-460, 430-470, 440-480, 450-490, and 456-497 of the sequence of SEQ ID NO: 7; and these fragments having one or more of the following features: one or more conservative amino acid substitutions (e.g., 1, 2, 3, 4, 5, 6, 7, 8, 9, 10, 11, 12, 13, 14, 15, or 16 conservative amino acid substitutions) in the sequence of SEQ ID NO: 7; one or more amino acids (e.g., 1, 2, 3, 4, 5, 6, 7, 8, 9, 10, 11, 12, 13, 14, 15, or 16 amino acids) truncated from the N and/or C-terminus of the sequence of SEQ ID NO: 7; and at least one flanking amino acid (e.g., 1, 2, 3, 4, 5, 6, 7, 8, 9, or 10 flanking amino acids) at the N- and/or C-terminus of the sequence of SEQ ID NO: 7.

By a "CT062 polypeptide" is meant a polypeptide that is substantially identical to the amino acid sequence of SEQ ID NO: 8. Desirably, a CT062 polypeptide has at least 80%, 85%, 90%, 95%, 99%, or even 100% identity to the amino acid sequence of SEQ ID NO: 8. Desirably, a CT062 polypeptide elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay).

By "fragment of a CT062 polypeptide" or a "CT062 fragment" is meant a polypeptide that is substantially identical to the sequence of SEQ ID NO: 9 (amino acids 23-412 of whole length CT062, SEQ ID NO: 8) containing fewer than 390 amino acids. Preferred CT062 fragments are between 7 and 389 amino acids in length (e.g., 7, 8, 9, 10, 11, 12, 13, 14, 15, 16, 17, 18, 19, 20, 40, 50, 100, or 150 amino acids in length). Desirably, a CT062 fragment elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay). Desirably, the fragment is fewer than 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 25, 20, 15, or 10 amino acids, and desirably, is immunogenic. A CT062 fragment may contain one or more conservative amino acid substitutions in the sequence of SEQ ID NO: 9. Additional desirable CT062 fragments contain one or more conservative amino acid substitutions in the sequence of SEQ ID NO: 9 and/or at least one flanking amino acid (e.g., 1, 2, 3, 4, 5, 6, 7, 8, 9, or 10 flanking amino acids) at the N- and/or C-terminus of the sequence of SEQ ID NO: 9. Other preferred CT062 fragments contain seven or more continuous amino acids of the sequence of SEQ ID NO: 9.

Non-limiting examples of a CT062 fragment include amino acids 1-40, 10-50, 20-60, 30-70, 40-80, 50-90, 60-100, 70-110, 80-120, 90-130, 100-140, 110-150, 120-160, 130-170, 140-180, 150-190, 160-200, 170-210, 180-220, 190-230, 200-240, 210-250, 220-260, 230-270, 240-280, 250-290, 260-300, 270-310, 280-320, 290-330, 300-340, 310-350, 320-360, 330-370, 340-380, and 350-390 of the sequence of SEQ ID NO: 9; and these fragments having one or more of the following features: one or more conservative amino acid substitutions (e.g., 1, 2, 3, 4, 5, 6, 7, 8, 9, 10, 11, 12, 13, 14, 15, or 16 conservative amino acid substitutions) in the sequence of SEQ ID NO: 9; one or more amino acids (e.g., 1, 2, 3, 4, 5, 6, 7, 8, 9, 10, 11, 12, 13, 14, 15, or 16 amino acids) truncated from the N and/or C-terminus of the sequence of SEQ ID NO: 9; and at least one flanking amino acid (e.g., 1, 2, 3, 4, 5, 6, 7, 8, 9, or 10 flanking amino acids) in the sequence of SEQ ID NO: 9.

By a "CT104 polypeptide" is meant a polypeptide that is substantially identical to the amino acid sequence of SEQ ID NO: 10. Desirably, a CT104 polypeptide has at least 80%, 85%, 90%, 95%, 99%, or even 100% identity to the amino acid sequence of SEQ ID NO: 10. Desirably, a CT104 polypeptide elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay).

By "fragment of a CT104 polypeptide" or a "CT 104 fragment" is meant a fragment of a CT104 polypeptide containing fewer than 298 amino acids. Preferred CT823 fragments are between 7 and 297 amino acids in length (e.g., 7, 8, 9, 10, 11, 12, 13, 14, 15, 16, 17, 18, 19, 20, 40, 50, 100, or 150 amino acids in length). Desirably, a CT104 fragment elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay). Desirably, the fragment is fewer than 298, 290, 280, 270, 260, 250, 240, 230, 220, 210, 200, 190, 180, 170, 160, 150, 140, 130, 120, 110, 100, 90, 80, 70, 60, 50, 40, 30, 25, 20, 15, or 10 amino acids, and desirably, is immunogenic. A CT104 fragment may contain one or more conservative amino acid substitutions in the sequence of SEQ ID NO: 10. Additional desirable CT104 fragments contain one or more conservative amino acid substitutions in the sequence of SEQ ID NO: 10 and/or at least one flanking amino acid (e.g., 1, 2, 3, 4, 5, 6, 7, 8, 9, or 10 flanking amino acids) at the N- and/or C-terminus of the sequence of SEQ ID NO: 10. Other preferred CT104 fragments contain seven or more continuous amino acids of the sequence of SEQ ID NO: 10.

Non-limiting examples of a CT104 fragment include amino acids 1-40, 10-50, 20-60, 30-70, 40-80, 50-90, 60-100, 70-110, 80-120, 90-130, 100-140, 110-150, 120-160, 130-170, 140-180, 150-190, 160-200, 170-210, 180-220, 190-230, 200-240, 210-250, 220-260, 230-270, 240-280, 250-290, and 258-298 of the sequence of SEQ ID NO: 10; and these fragments having one or more of the following features: one or more conservative amino acid substitutions (e.g., 1, 2, 3, 4, 5, 6, 7, 8, 9, 10, 11, 12, 13, 14, 15, or 16 conservative amino acid substitutions) in the sequence of SEQ ID NO: 10; one or more amino acids (e.g., 1, 2, 3, 4, 5, 6, 7, 8, 9, 10, 11, 12, 13, 14, 15, or 16 amino acids) truncated from the N and/or C-terminus of the sequence of SEQ ID NO: 10; and at least one flanking amino acid (e.g., 1, 2, 3, 4, 5, 6, 7, 8, 9, or 10 flanking amino acids) at the N- and/or C-terminus of the sequence of SEQ ID NO: 10.

By a "CT111 polypeptide" is meant a polypeptide that is substantially identical to the amino acid sequence of SEQ ID NO: 11. Desirably, a CT111 polypeptide has at least 80%, 85%, 90%, 95%, 99%, or even 100% identity to the amino acid sequence of SEQ ID NO: 11. Desirably, a CT111 polypeptide elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay).

By "fragment of a CT111 polypeptide" or a "CT111 fragment" is meant a fragment of a CT111 polypeptide containing fewer than 102 amino acids. Preferred CT111 fragments are between 7 and 101 amino acids in length (e.g., 7, 8, 9, 10, 11, 12, 13, 14, 15, 16, 17, 18, 19, 20, 40, 50, 100, or 150 amino acids in length). Desirably, a CT111 fragment elicits at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay). Desirably, the fragment is fewer than 102, 100, 90, 80, 70, 60, 50, 40, 30, 25, 20, 15, or 10 amino acids, and desirably, is immunogenic. A CT111 fragment may contain one or more conservative amino acid substitutions in the sequence of SEQ ID NO: 11. Additional desirable CT111 fragments contain one or more conservative amino acid substitutions in the sequence of SEQ ID NO: 11 and/or at least one flanking amino acid (e.g., 1, 2, 3, 4, 5, 6, 7, 8, 9, or 10 flanking amino acids) at the N- and/or C-terminus of the sequence of SEQ ID NO: 11. Other preferred CT111 fragments contain seven or more continuous amino acids of the sequence of SEQ ID NO: 11.

Non-limiting examples of a CT111 fragment include amino acids 1-40, 10-50, 20-60, 30-70, 40-80, 50-90, 60-100, and 60-102 of the sequence of SEQ ID NO: 11; and these fragments having one or more of the following features: one or more conservative amino acid substitutions (e.g., 1, 2, 3, 4, 5, 6, 7, 8, 9, 10, 11, 12, 13, 14, 15, or 16 conservative amino acid substitutions) in the sequence of SEQ ID NO: 11; one or more amino acids (e.g., 1, 2, 3, 4, 5, 6, 7, 8, 9, 10, 11, 12, 13, 14, 15, or 16 amino acids) truncated from the N and/or C-terminus of the sequence of SEQ ID NO: 11; and at least one flanking amino acid (e.g., 1, 2, 3, 4, 5, 6, 7, 8, 9, or 10 flanking amino acids) at the N- and/or C-terminus of the sequence of SEQ ID NO: 11.

By "substantially identical" is meant a polypeptide exhibiting at least 50%, desirably 60%, 70%, 75%, or 80%, more desirably 85%, 90%, or 95%, and most desirably 99% amino acid sequence identity to a reference amino acid sequence. The length of comparison sequences will generally be at least 10 amino acids, desirably at least 15 contiguous amino acids, more desirably at least 20, 25, 50, 75, 90, 100, 150, 200, 250, 300, or 350 contiguous amino acids, and most desirably the full-length amino acid sequence.

Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

Multiple sequences may also be aligned using the Clustal W(1.4) program (produced by Julie D. Thompson and Toby Gibson of the European Molecular Biology Laboratory, Germany and Desmond Higgins of European Bioinformatics Institute, Cambridge, UK) by setting the pairwise alignment mode to "slow," the pairwise alignment parameters to include an open gap penalty of 10.0 and an extend gap penalty of 0.1, as well as setting the similarity matrix to "blosum." In addition, the multiple alignment parameters may include an open gap penalty of 10.0, an extend gap penalty of 0.1, as well as setting the similarity matrix to "blosum," the delay divergent to 40%, and the gap distance to 8.

By "conservative amino acid substitution," as used herein, is meant replacement, in an amino acid sequence, of an amino acid for another within a family of amino acids that are related in the chemical nature of their side chains.

Genetically encoded amino acids can be divided into four families: acidic (aspartate, glutamate); basic (lysine, arginine, histidine); nonpolar (alanine, valine, leucine, isoleucine, proline, phenylalanine, methionine, tryptophan); and uncharged polar (glycine, asparagine, glutamine, cysteine, serine, threonine, tyrosine). Phenylalanine, tryptophan, and tyrosine are sometimes grouped as aromatic amino acids. In similar fashion, the amino acids can also be separated into the following groups: acidic (aspartate, glutamate); basic (lysine, arginine, histidine); aliphatic (glycine, alanine, valine, leucine, isoleucine, serine, threonine), with serine and threonine optionally grouped separately as aliphatic-hydroxyl; aromatic (phenylalanine, tyrosine, tryptophan); amide (asparagine, glutamine); and sulfur-containing (cysteine, methionine).

Whether a change in the amino acid sequence results in a functional homolog can be determined by assessing the ability of the variant peptide to function in a fashion similar to the wild-type protein using standard methods such as the assays described herein. For example, $C.$ $trachomatis$-specific CD4$^+$ or CD8$^+$ cells may be used to determine whether specific $C.$ $trachomatis$ polypeptides or fragments thereof, are immunogenic. Desirable embodiments of the invention, include at least one conservative amino acid substitution in the amino acid sequence of SEQ ID NO: 1, 2, 3, 4, 5, 6, 7, 8, 9, 10, or 11; and more desirably 1, 2, 3, 4, 5, 6, 7, 8, 9, or 10 conservative amino acid substitutions in the sequence of SEQ ID NO: 1, 2, 3, 4, 5, 6, 7, 8, 9, 10, or 11.

By "flanking amino acid" is meant an amino acid in a polypeptide sequence that is immediately adjacent to the N- or C-terminus of a particular defined sequence. Desirably, a flanking amino acid is present on the N- and/or C-terminus of the amino acid sequence of SEQ ID NO: 1, 2, 3, 4, 5, 6, 7, 8, 9, 10, or 11, or a fragment thereof; and more desirably, 1, 2, 3, 4, 5, 6, 7, 8, 9, or flanking amino acids are present at the N- and/or C-terminus of the amino acid sequence of SEQ ID NO: 1, 2, 3, 4, 5, 6, 7, 8, 9, 10, or 11, or fragment thereof.

As used herein "fusion protein" refers to a polypeptide consisting of (1) a CT491 polypeptide, CT491 fragment, CT601 polypeptide, CT601 fragment, CT781 polypeptide, CT781 fragment, CT687 polypeptide, CT687 fragment, CT732 polypeptide, CT732 fragment, CT808 polypeptide, CT808 fragment, CT823 polypeptide, CT823 fragment, CT062 polypeptide, CT062 fragment, CT104 polypeptide, CT104 fragment, CT111 polypeptide, or CT111 fragment of the present invention; and (2) a fusion partner.

As used herein "fusion partner" refers to a heterologous sequence that can be fused to a CT491 polypeptide, CT491 fragment, CT601 polypeptide, CT601 fragment, CT781 polypeptide, CT781 fragment, CT687 polypeptide, CT687 fragment, CT732 polypeptide, CT732 fragment, CT808 polypeptide, CT808 fragment, CT823 polypeptide, CT823 fragment, CT062 polypeptide, CT062 fragment, CT104 polypeptide, CT104 fragment, CT111 polypeptide, or CT111 fragment of the present invention. Desirably, the fusion partner provides a new function or activity to the CT491 polypeptide, CT491 fragment, CT601 polypeptide, CT601 fragment, CT781 polypeptide, CT781 fragment, CT687 polypeptide, CT687 fragment, CT732 polypeptide, CT732 fragment, CT808 polypeptide, CT808 fragment, CT823 polypeptide, CT823 fragment, CT062 polypeptide, CT062 fragment, CT104 polypeptide, CT104 fragment, CT111 polypeptide, or CT111 fragment. Examples of fusion partners are described herein and include detection markers, DNA binding domains, gene activation domains, stabilizing domains, or sequences which aid in production or purification of the protein.

As used herein "immune response" refers to the activation of an organism's immune system in response to an antigen or infectious agent. In vertebrates, this may include, but is not limited to, one or more of the following: naïve B cell maturation into memory B cells; antibody production by plasma cells (effector B cells); induction of cell-mediated immunity; activation and cytokine release by $CD4^+$ T cells; activation and cytokine release of $CD8^+$ T cells; cytokine recruitment and activation of phagocytic cells (e.g., macrophages, neutrophils, eosinophils); and/or complement activation.

By "immunogenic" is meant any substance that is capable of inducing an immune response in a subject.

By "non-antigenic" is meant any peptide which elicits the lowest level of interferon-γ production compared to other tested peptides in the T-lymphocyte assays described in the Examples. For example, a non-antigenic peptide elicits a level of interferon-γ production that is at least 4-fold lower (e.g., 5-fold, 6-fold, 7-fold, or 8-fold lower) than the level of interferon-γ production that is elicited using an antigenic peptide. The non-antigenic peptide may be a human peptide, a *Chlamydia trachomatis* peptide, or a peptide from any other microorganism. Non-limiting examples of non-antigenic peptides include *Listeria monocytogenes* listeriolysin O (LLO), amino acids 91-99 (GYKDGNEYI; SEQ ID NO: 12); ovalbumin (OVA), amino acids 257-264 (SIINFEKL; SEQ ID NO: 13); and lymphocytic choriomeningitis virus (LCMV) nucleoprotein (NP), amino acids 118-126 (RPQASGVYM; SEQ ID NO: 14).

By "pharmaceutically acceptable salt" is meant any nontoxic acid addition salt or metal complex used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid, phosphoric acid, or the like. Metal complexes include zinc, iron, and the like.

By "pharmaceutically acceptable carrier" is meant any solution used to solubilize and deliver an agent to a subject. A desirable pharmaceutically acceptable carrier is saline. In desirable embodiments, a pharmaceutically acceptable carrier includes an adjuvant. Exemplary adjuvants are described herein. Other physiologically acceptable carriers and their formulations are known to one skilled in the art and described, for example, in Remington's Pharmaceutical Sciences, (20th edition), ed. A. Gennaro, 2003, Lippincott Williams & Wilkins.

By "isolated" is meant a protein (or a fragment thereof) that has been separated from components that naturally accompany it. Typically, the polypeptide is substantially isolated when it is at least 60%, by weight, free from the proteins and naturally occurring organic molecules with which it is naturally associated. The definition also extends to a polypeptide separated from its flanking amino acids (e.g., for an amino acid sequence, isolated refers to a sequence that is free from the flanking amino acids with which the sequence is naturally associated in a polypeptide). Preferably, the polypeptide is at least 75%, more preferably at least 90%, and most preferably at least 99%, by weight, isolated. An isolated polypeptide may be obtained by standard techniques, for example, by extraction from a natural source (e.g., purification from a cell infected with *C. trachomatis*), by expression of a recombinant nucleic acid encoding a CT491 polypeptide, CT491 fragment, CT601 polypeptide, CT601 fragment, CT781 polypeptide, CT781 fragment, CT687 polypeptide, CT687 fragment, CT732 polypeptide, CT732 fragment, CT808 polypeptide, CT808 fragment, CT823 polypeptide, CT823 fragment, CT062 polypeptide, CT062 fragment, CT104 polypeptide, CT104 fragment, CT111 polypeptide, or CT111 fragment; or fusion protein thereof, by chemically synthesizing the polypeptide. Purity can be measured by any appropriate method, e.g., by column chromatography, polyacrylamide gel electrophoresis, or HPLC analysis.

By a "therapeutically effective amount" is meant the amount of a immunogenic compound (e.g., polypeptide, fragment, fusion protein, or vaccine) required to generate in a subject one or more of the following effects: an immune response; a decrease in the level of *Chlamydia* infection (e.g., a reduction of at least 5%, 10%, 20%, or 30%; more desirably 40%, 50%, 60%, or 70%; and most desirably 80% or 90%); a decrease (e.g., at least a 10%, 20%, 30%, 40%, 50%, 60%, 70%, 80%, 90%, or even 100% reduction) in one or more symptoms of *C. trachomatis* infection in a patient (e.g., cystitis, pain during urination, pain or bleeding during or after sexual intercourse, abdominal pains, irregular menstrual bleeding, painful swelling and irritation of the eyes, white/cloudy and watery penile discharge, fever, lower back pain, and swollen or painful testicles); or increased resistance to a new *Chlamydia* infection (e.g., an increase of at least 5%, 10%, 20%, 30%, 40%, or 50%; more desirably 60%, 70%, 80%, or 90%; or most desirably 100%, 200%, or 300%).

BRIEF DESCRIPTION OF THE DRAWINGS

FIG. 1 is the complete amino acid sequence of the polypeptide CT491 (SEQ ID NO: 1) (Genbank Accession number NP_220005).

FIG. 2 is the complete amino acid sequence of the polypeptide CT601 (SEQ ID NO: 2) (Genbank Accession number NP_220117).

FIG. 3 is the complete amino acid sequence of the polypeptide CT687 (SEQ ID NO: 3) (Genbank Accession number NP_220206).

FIG. 4 is the complete amino acid sequence of the polypeptide CT732 (SEQ ID NO: 4) (Genbank Accession number NP_220251).

FIG. 5 is the complete amino acid sequence of the polypeptide CT781 (SEQ ID NO: 5) (Genbank Accession number NP_220300).

FIG. 6 is the complete amino acid sequence of the polypeptide CT808 (SEQ ID NO: 6) (Genbank Accession number NP_220328).

FIG. 7 is the complete amino acid sequence of the polypeptide CT823 (SEQ ID NO: 7) (Genbank Accession number NP_220344).

FIG. 8 is the full length amino acid sequence of the polypeptide CT062 (SEQ ID NO: 8) (Genebank Accession number NP_219565).

FIG. 9 is the partial amino acid sequence of the polypeptide CT062 (SEQ ID NO: 9) (amino acids 23-412 of Genbank Accession number NP 219565).

FIG. 10 is the full length amino acid sequence of the polypeptide CT104 (SEQ ID NO: 10) (Genbank Accession number NP_219607).

FIG. 11 is the full length amino acid sequence of the polypeptide CT111 (SEQ ID NO: 11) (Genbank Accession number NP_219614).

DETAILED DESCRIPTION

Previous attempts to develop a Chlamydial vaccine have met with little success (Cotter et al., *Infect. Immun.* 63:4704-4714, 1995) (Pal et al., *Vaccine* 17:459-465, 1999) (Pal et al., *Infect. Immun.* 65:3361-3369, 1997) (Su et al., *Vaccine* 13:1023-1032, 1995) (Taylor et al., *Invest. Opthalmol. Vis. Sci.* 29:1847-1853, 1988) (Zhang et al., *J. Infect. Dis.* 176: 1035-1040, 1997). Subunit vaccines have the potential to be able to control many important human pathogens which have thus far resisted classical vaccination strategies.

*Chlamydia trachomatis* is a human pathogen against which a protective vaccine has not been developed even though it is a significant burden on human society. It is the most common bacterial cause of sexually transmitted disease in the United States. Chronic inflammation in the female genital tract caused by *C. trachomatis* can lead to serious pathologies such as pelvic inflammatory disease and ectopic pregnancy. *C. trachomatis* is also the most common cause of preventable blindness worldwide with an estimated 1-1.5 million people currently blind from the disease.

Use of classical vaccinology methods did not yield a successful vaccine against *C. trachomatis* pathogen because immunization with killed bacteria leads to an increase in the severity of the pathologies associated with the disease and the lack of a genetic system to manipulate the bacterium has prevented the development of attenuated *Chlamydia* strains. A subunit vaccine in which specific proteins from *C. trachomatis* are used to elicit an immune response has the potential to overcome the barriers to a successful vaccine by eliciting responses to protective antigens while avoiding the pathological responses associated with immunization with the entire organism. To make a successful *C. trachomatis* subunit vaccine, the proteins in the *C. trachomatis* proteome that elicit protective immune responses must be identified.

We report here the identification of new *C. trachomatis* proteins that elicit CD8$^+$ T-cell responses during *C. trachomatis* infection.

The immunogenic *Chlamydia* peptides of the present invention were identified in an assay utilizing *C. trachomatis*-specific CD8$^+$ T cells, and an expression library of genomic sequences from *C. trachomatis* serovar D. A detailed description of the assay and its components is provided below.

The invention features CT491, CT601, CT687, CT732, CT781, CT808, CT823, CT062, CT104, and CT111 polypeptides, polypeptide fragments, and fusion proteins. The invention further features compositions, vaccines (e.g., DNA vaccines), and kits containing one or more CT491, CT601, CT687, CT732, CT781, CT808, CT823, CT062, CT104, or CT111 polypeptide, polypeptide fragment, or fusion protein (or a polynucleotide sequence encoding a polypeptide, polypeptide fragment, or fusion protein of the present invention).

Methods for the addition of flanking amino acids to the amino or carboxy ends of a specific protein sequence are well known in the art. The flanking amino acids added may be the naturally adjoining sequences present in the full-length sequence of the naturally-occurring polypeptide (e.g., for a CT491 fragment, the adjoining sequence in the sequence of SEQ ID NO: 1; for a CT601 fragment, the adjoining sequence in the sequence of SEQ ID NO: 2; for a CT687 fragment, the adjoining sequence in the sequence of SEQ ID NO: 3; for a CT732 fragment, the adjoining sequence in the sequence of SEQ ID NO: 4; for a CT781 fragment, the adjoining sequence in the sequence of SEQ ID NO: 5; for a CT808 fragment, the adjoining sequence in the sequence of SEQ ID NO: 6; for a CT823 fragment, the adjoining sequence in the sequence of SEQ ID NO: 7; for a CT062 fragment, the adjoining sequence in the sequence of SEQ ID NO: 8; for a CT104 fragment, the adjoining sequence in the sequence of SEQ ID NO: 10; for a CT111 fragment, the adjoining sequence in the sequence of SEQ ID NO: 11), or may comprise any other amino acid sequence.

In addition, the invention also provides fusion proteins consisting of (1) any of the CT491, CT601, CT687, CT732, CT781, CT808, CT823, CT062, CT104, or CT111 polypeptides or polypeptide fragments, and (2) a fusion partner. A fusion partner is a heterologous protein sequence that may provide an additional function or activity to the fragment of the invention. For example, a fusion partner may be detected directly or indirectly (e.g., green fluorescent protein (GFP), hemagglutinin, or alkaline phosphatase), provide a DNA binding domain (e.g., GAL4 or LexA), provide a gene activation domain (e.g., GAL4 or VP16), stabilize the polypeptide, or facilitate its production or purification (e.g., His$_6$, a myc tag, streptavidin, a SIINFEKL epitope (SEQ ID NO: 12), or a secretion signal).

The fusion partner may also contain sequences which provide immunostimulatory function, examples include interleukin-2 (Fan et al., *Acta Biochim. Biophys. Sin.* 38:683-690, 2006), immunoglobulin (e.g., IgG, IgM, IgE, or IgA), Toll-like receptor-5 flagellin (Huleatt et al., *Vaccine* 8:763-775, 2007), simian immunodeficiency virus Tat (Chen et al., *Vaccine* 24:708-715, 2006), or fibrinogen-albumin-IgG receptor of group C streptococci (Schulze et al., *Vaccine* 23:1408-1413, 2005). In addition, fusion partner sequences may be added to enhance solubility or increase half-life, for example, hydrophilic amino acid residues (Murby et al., *Eur. J. Biochem.* 230:38-44, 1995), glycosylation sequences (Sinclair and Elliott, *J. Pharm. Sci.* 94:1626-1635, 2005), or the carboxy terminus of human chorionic gonadotropin or thrombopoeitin (Lee et al., *Biochem. Biophys. Res. Comm.* 339:380-

385, 2006). Methods for the addition of these flanking sequences are known in the art and further described herein.

In addition, methods for introducing conservative amino acid substitutions into a polypeptide sequence are also known in the art. Amino acids within the sequence of SEQ ID NO: 1, 2, 3, 4, 5, 6, 7, 8, 9, 10, or 11 can be replaced with other amino acids having similar chemical characteristics. For example, a conservative substitution is replacing one acidic amino acid for another (e.g., aspartate for glutamate, or vice versa). Another example, is replacing one basic amino acid for another (lysine for histidine, or vice versa).

Methods for removing amino acids from the amino and/or carboxy end of a polypeptide sequence are also known in the art. Amino acids desirably are removed from the amino and/or carboxy end of a protein fragment of SEQ ID NO: 1, 2, 3, 4, 5, 6, 7, 8, 9, 10, or 11.

The specific polypeptides, polypeptide fragments, or fusion proteins disclosed herein can be assayed for their immunogenicity using standard methods as described, for instance, in the Example below.

CT491, CT601, CT687, CT732, CT781, CT808, CT823, CT062, CT104, and CT111 Polypeptide, Polypeptide Fragment, or Fusion Protein Expression The CT491, CT601, CT687, CT732, CT781, CT808, CT823, CT062, CT104, and CT111 polypeptides, polypeptide fragments, or fusion proteins of the present invention may be produced by transformation of a suitable host cell with a polynucleotide molecule encoding the polypepetide, polypeptide fragment, or fusion protein in a suitable expression vehicle.

Those skilled in the field of molecular biology will understand that any of a wide variety of expression systems may be used to provide the CT491, CT601, CT687, CT732, CT781, CT808, CT823, CT062, CT104, and CT111 polypeptides, polypeptide fragments, or fusion proteins disclosed herein. The precise host cell used is not critical to the invention. CT491, CT601, CT687, CT732, CT781, CT808, CT823, CT062, CT104, and CT111 polypeptides, polypeptide fragments, or fusion proteins may be produced in prokaryotic host (e.g., E. coli) or in a eukaryotic host (e.g., S. cerevisiae, insect cells, e.g., Sf21 cells, or mammalian cells, e.g., NIH 3T3, HeLa, or preferably COS cells). Such cells are available from a wide range of sources (e.g., the American Type Culture Collection, Manassas, Va.). The method of transformation or transfection and the choice of expression vehicle will depend on the host system selected. Transformation and transfection methods are described, e.g., in Kucherlapati et al. (*CRC Crit. Rev. Biochem.* 16:349-379, 1982) and in *DNA Transfer to Cultured Cells* (eds., Ravid and Freshney, Wiley-Liss, 1998); and expression vehicles may be chosen from those provided, e.g., in *Vectors: Expression Systems Essential Techniques* (ed., Jones, Wiley & Sons Ltd., 1998).

Once the recombinant polypeptide, polypeptide fragment, or fusion protein is expressed, it can be isolated, e.g., using affinity chromatography. In one example, an antibody raised against a CT491, CT601, CT687, CT732, CT781, CT808, CT823, CT062, CT104, or CT111 polypeptide, polypeptide fragment, or fusion protein may be attached to a column and used to isolate the recombinant polypeptide, polypeptide fragment, or fusion protein. Lysis and fractionation of polypeptide-, polypeptide fragment-, or fusion protein-harboring cells prior to affinity chromatography may be performed by standard methods (see, e.g., *Methods in Enzymology*, volume 182, eds., Abelson, Simon, and Deutscher, Elsevier, 1990).

Once isolated, the recombinant CT491, CT601, CT687, CT732, CT781, CT808, CT823, CT062, CT104, and CT111 polypeptides, polypeptide fragments, or fusion proteins can, if desired, be further purified, e.g., by high performance liquid chromatography (see e.g., Fisher, *Laboratory Techniques in Biochemistry and Molecular Biology*, eds., Work and Burdon, Elsevier, 1980; and Scopes, *Protein Purification: Principles and Practice*, Third Edition, ed., Cantor, Springer, 1994).

The CT491, CT601, CT687, CT732, CT781, CT808, CT823, CT062, CT104, and CT111 polypeptides, polypeptide fragments, or fusion proteins can also be produced by chemical synthesis (e.g., by the methods described in *Solid Phase Peptide Synthesis*, 2nd ed., 1984, The Pierce Chemical Co., Rockford, Ill.; and *Solid-Phase Synthesis: A Practical Guide*, ed., Kates and Albericio, Marcel Dekker Inc., 2000).

For production of stable cell lines expressing the polypeptides described herein, PCR-amplified nucleic acids encoding any of the CT491, CT601, CT687, CT732, CT781, CT808, CT823, CT062, CT104, or CT111 polypeptides, polypeptide fragments, or fusion proteins of the present invention may be cloned into the restriction site of a derivative of a mammalian expression vector. For example, KA, which is a derivative of pcDNA3 (Invitrogen, Carlsbad, Calif.) contains a DNA fragment encoding an influenza virus hemagglutinin (HA). Alternatively, vector derivatives encoding other tags, such as c-myc or poly-histidine tags, can be used.

Vaccine Production

The invention also provides for a vaccine composition including one or more of the CT491, CT601, CT687, CT732, CT781, CT808, CT823, CT062, CT104, or CT111 polypeptides, polypeptide fragments, or fusion proteins of the present invention. The invention further provides a vaccine composition including one or more of any of the polypeptides, polypeptide fragments, or fusion proteins of the present invention combined with one or more antigens disclosed in U.S. Patent Application Nos. 60/775,462; 60/817,471; and 60/963,215; herein incorporated by reference in their entirety.

The invention also provides DNA vaccines which contain polynucleotide sequences encoding one or more of the CT491, CT601, CT687, CT732, CT781, CT808, CT823, CT062, CT104, or CT111 polypeptides, polypeptide fragments, or fusion proteins of the present invention. The invention further provides DNA vaccines which contain polynucleotide sequences encoding one or more of any of the polypeptides, polypeptide fragments, or fusion proteins of the present invention, and one or more polynucleotide sequences encoding any of the polypeptides, polypeptide fragments, or fusion proteins disclosed in U.S. Patent Application Nos. 60/775,462; 60/817,471; and 60/963,215; herein incorporated by reference in their entirety.

Preferred polypeptides, polypeptide fragments, or fusion proteins, for use in a vaccine composition elicit at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay). Likewise, preferred polynucleotide sequences for use in a DNA vaccine contain polynucleotide sequences encoding CT491, CT601, CT687, CT732, CT781, CT808, CT823, CT062, CT104, or CT111 polypeptides, polypeptide fragments, or fusion proteins of the present invention which elicit at least a 3-, 4-, 5-, 6-, 7-, 8-, 10-, 20-, 30-, 40-, 50-, 60-, 70-, 80-, 90-, 100-, 200-, or 500-fold increase in interferon-γ production from a population of T-lymphocytes compared to the level of interferon-γ production from T-lymphocytes treated with a non-antigenic peptide in the same assay (e.g., a peptide which elicits the lowest measurable value of IFN-γ in the same assay). The invention further includes a method of inducing an immunological response in a subject, particularly a human, the method including inoculating a subject with one or more CT491, CT601, CT687, CT732, CT781, CT808, CT823, CT062, CT104, or CT111 polypeptide, polypeptide fragment, or fusion protein, or a DNA vaccine containing a polynucleotide sequence encoding one or more CT491, CT601, CT687, CT732, CT781, CT808, CT823, CT062, CT104, or CT111 polypeptide, polypeptide fragment, or fusion protein disclosed herein, in a suitable carrier for the purpose of inducing an immune response to prevent or protect a subject from infection, desirably bacterial infection, and most desirably, *C. trachomatis* infection. In addition to the polypeptides, polypeptide fragments, fusion proteins, and vaccines of the present invention, a subject may also be inoculated with one or more of the polypeptides, polypeptide fragments, fusion proteins, and vaccines of U.S. Patent Application Nos. 60/775,462; 60/817,471; and 60/963,215; herein incorporated by reference in their entirety.

The administration of this immunological composition of the present invention (e.g., DNA vaccine) may be used either therapeutically in subjects already experiencing an infection, or may be used prophylactically to prevent an infection. In addition, the above described vaccines can also be administered to subjects to generate polyclonal antibodies (purified or isolated from serum using standard methods) that may be used to passively immunize a subject. These polyclonal antibodies can also serve as immunochemical reagents.

The preparation of vaccines that contain immunogenic polypeptides is known to one skilled in the art. The CT491, CT601, CT687, CT732, CT781, CT808, CT823, CT062, CT104, or CT111 polypeptides, polypeptide fragments, or fusion proteins of the present invention may serve as an antigen for vaccination. Both the protein-based vaccines described herein and DNA vaccines encoding the polypeptides, polypeptide fragments, or fusion proteins of the present invention may be delivered to a subject in order to induce an immunological response comprising the production of antibodies, or, in particular, a $CD4^+$ and/or $CD8^+$ T cell response in a subject.

Protein-based vaccines are typically prepared from one or more purified recombinant CT491, CT601, CT687, CT732, CT781, CT808, CT823, CT062, CT104, or CT111 polypeptide, polypeptide fragment, or fusion protein of the present invention in a physiologically acceptable diluent vehicle such as water, phosphate-buffered saline (PBS), acetate-buffered saline (ABS), Ringer's solution, or the like to form an aqueous composition. The diluent vehicle can also include oleaginous materials such as squalane, or squalene as is discussed below.

Vaccine antigens are usually combined with a pharmaceutically acceptable carrier, which includes any carrier that does not include the production of antibodies harmful to the subject receiving the carrier. Suitable carriers typically comprise large macromolecules that are slowly metabolized, such as proteins, polysaccharides, polylactic acids, polyglycolic acids, polymeric amino acids, amino acid copolymers, lipid aggregates, and inactive virus particles. Such carriers are well known to those skilled in the art. These carriers may also function as adjuvants.

The CT491, CT601, CT687, CT732, CT781, CT808, CT823, CT062, CT104, or CT111 polypeptides, polypeptide fragments, or fusion proteins of the present invention may be mixed with excipients that are pharmaceutically acceptable and compatible with the immunogenic polypeptide, polypeptide fragment, or fusion protein. Suitable excipients are, for example, water, saline, dextrose, glycerol, ethanol, or the like and combinations thereof. In addition, if desired, a vaccine can contain minor amounts of auxiliary substances such as wetting or emulsifying agents, or pH buffering agents that enhance the immunogenic effectiveness of the composition.

A protein-based vaccine advantageously also includes an adjuvant. Suitable adjuvants for vaccines of the present invention comprise those adjuvants that are capable of enhancing the B cell and/or T cell response (e.g., $CD4^+$ and/or $CD8^+$ T cell response) to the immunogenic polypeptide or fragment of the present invention. Adjuvants are well known in the art (see, e.g., *Vaccine Design-The Subunit and Adjuvant Approach*, 1995, Pharmaceutical Biotechnology, Volume 6, Eds. Powell and Newman, Plenum Press, New York and London).

Preferred adjuvants for use with the immunogens of the present invention include aluminum or calcium salts (e.g., hydroxide or phosphate salts). A desirable adjuvant is an aluminum hydroxide gel such as Alhydrogel™. For aluminum hydroxide gels (alum), the immunogenic polypeptide fragment or fusion protein is admixed with the adjuvant so that between 50 to 800 μg of aluminum are present per dose, and preferably, between 400 and 600 μg are present.

Another adjuvant for use with an immunogenic polypeptide, polypeptide fragment, or fusion protein of the present invention is an emulsion. An emulsion can be an oil-in-water emulsion or a water-in-oil emulsion. In addition to the immunogenic polypeptide, polypeptide fragment, or fusion protein, such emulsions comprise an oil phase of squalene, squalane, or the like, as are well known, and a dispersing agent. Non-ionic dispersing agents are preferred and such materials include mono- and di-$C_{12}$-$C_{24}$-fatty acid esters of sorbitan and mannide such as sorbitan mono-stearate, sorbitan mono-oleate, and mannide mono-oleate. An immunogen-containing emulsion is administered as an emulsion.

Desirably, such emulsions are water-in-oil emulsions that comprise squalene and mannide mono-oleate (Arlacel™ A), optionally with squalane, emulsified with the immunogenic polypeptide fragment or fusion protein in an aqueous phase. Well-known examples of such emulsions include Montanide™ ISA-720 and Montanide™ ISA-703 (Seppic, Castres, France), each of which is understood to contain both squalene and squalane, with squalene predominating in each, but to a lesser extent in Montanide™ ISA-703. Desirably, Montanide™ ISA-720 is used, and a ratio of oil-to-water of 7:3 (w/w) is used. Other preferred oil-in-water emulsion adjuvants include those disclosed in WO 95/17210 and EP 0399842, herein incorporated by reference.

The use of small molecule adjuvants is also contemplated herein. One type of small molecule adjuvant useful herein is a 7-substituted-8-oxo- or 8-sulfo-guanosine derivative described in U.S. Pat. Nos. 4,539,205; 4,643,992; 5,011,828; and 5,093,318; herein incorporated by reference. Of these materials, 7-allyl-8-oxoguanosine (loxoribine) is particularly preferred. Loxoribine has been shown to be particularly effective in inducing an immunogen-specific response.

Additional useful adjuvants include monophosphoryl lipid A (MPL) available from Corixa Corp. (see, U.S. Pat. No. 4,987,237), CPG available from Coley Pharmaceutical Group, QS21 available from Aquila Biopharmaceuticals, Inc., SBAS2 available from SmithKline Beecham, the so-called muramyl dipeptide analogues described in U.S. Pat. No. 4,767,842, and MF59 available from Chiron Corp. (see, U.S. Pat. Nos. 5,709,879 and 6,086,901). Further adjuvants include the active saponin fractions derived from the bark of the South American tree *Quillaja Saponaria Molina* (e.g., Quil™ A). Derivatives of Quil™ A, for example QS21 (an HPLC purified fraction derivative of Quil™ A), and the method of its production is disclosed in U.S. Pat. No. 5,057, 540. In addition to QS21 (known as QA21), other fractions such as QA17 are also disclosed.

3-De-O-acylated monophosphoryl lipid A is a well-known adjuvant manufactured by Ribi Immunochem. The adjuvant contains three components extracted from bacteria: monophosphoryl lipid (MPL) A, trehalose dimycolate (TDM), and cell wall skeleton (CWS) in a 2% squalene/Tween™ 80 emulsion. This adjuvant can be prepared by the methods taught in GB 2122204B. A preferred form of 3-de-O-acylated monophosphoryl lipid A is in the form of an emulsion having a small particle size of less than 0.2 µm in diameter (EP 0689454 B1).

The muramyl dipeptide adjuvants include N-acetyl-muramyl-L-threonyl-D-isoglutamine (thr-MDP; U.S. Pat. No. 4,606,918), N-acetyl-nor-muramyl-L-alanyl-D-isoglutamine (CGP 11637, referred to as nor-MDP), and N-acteryl-muramyl-L-alanyl-D-isoglutaminyl-L-alanine-2-(1',2'-dipalmitoyl-sn-glycero-3-hydroxyphosphoryloxy)-ethylamin (CGP) 1983A, referred to as MTP-PE.

Desirable adjuvant mixtures include combinations of 3D-MPL and QS21 (EP0671948 B1), oil-in-water emulsions comprising 3D-MPL and QS21 (WO 95/17210, PCT/EP98/05714), 3D-MPL formulated with other carriers (EP 0689454 B1), QS21 formulated in cholesterol-containing liposomes (WO 96/33739), or immunostimulatory oligonucleotides (WO 96/02555). Alternative adjuvants include those described in WO 99/52549 and non-particulate suspensions of polyoxyethylene ether (UK Patent Application No. 9807805.8).

Adjuvants are utilized in an adjuvant amount, which can vary with the adjuvant, mammal, and the immunogenic CT491, CT601, CT687, CT732, CT781, CT808, CT823, CT062, CT104, and CT111 polypeptide, polypeptide fragment, or fusion protein. Typical amounts can vary from about 1 µg to about 1 mg per immunization. Those skilled in the art know that appropriate concentrations or amounts can be readily determined.

The present invention also provides DNA vaccines containing polynucleotide sequences encoding the one or more of the polypeptides, polypeptide fragments, and fusion proteins of the present invention. Methods for the preparation of DNA vaccines which contain polynucleotide sequences encoding the CT491, CT601, CT687, CT732, CT781, CT808, CT823, CT062, CT104, or CT111 polypeptides, polypeptide fragments, or fusion proteins of the present invention are known in the art. For example, the polynucleotide sequences encoding the CT491, CT601, CT687, CT732, CT781, CT808, CT823, CT062, CT104, or CT111 polypeptides, polypeptide fragments, or fusion proteins of the present invention may be placed into virus-based vectors, which transfer the CT491, CT601, CT687, CT732, CT781, CT808, CT823, CT062, CT104, or CT111 polypeptide-, polypeptide fragment-, or fusion protein-encoding polynucleotide sequence (e.g., DNA or RNA) into a cell, such that the encoded polypeptide, polypeptide fragment, or fusion protein is expressed in the cell. Different viral-based vectors that may be used to deliver the CT491, CT601, CT687, CT732, CT781, CT808, CT823, CT062, CT104, or CT111 polypeptide-, polypeptide fragment-, or fusion protein-encoding polynucleotide sequences include adenoviral vectors and adeno-associated virus-derived vectors, retroviral vectors, Moloney Murine Leukemia virus-based vectors, Spleen Necrosis Virus-based vectors, Friend Murine Leukemia-based vectors, lentivirus-based vectors (Lois et al., *Science*, 295:868-872, 2002), papova virus-based vectors (e.g., SV40 viral vectors), Herpes Virus-based vectors, viral vectors that contain or display the Vesicular Stomatitis Virus G-glycoprotein Spike, Semliki-Forest virus-based vectors, Hepadnavirus-based vectors, and Baculovirus-based vectors. Additional, exemplary DNA vaccine vectors (not intended as limiting) may be found in "Gene Transfer and Expression in Mammalian Cells," Savvas C. Makrides (Ed.), Elsevier Science Ltd, 2003. The DNA vaccine may be provided to a subject in combination with one or more acceptable diluent vehicles, pharmaceutically acceptable carriers, adjuvants, excipients, wetting or emulsifying agents, or pH buffering agents (examples provided herein) and/or one or more nucleic acid delivery agents (e.g., polymer, lipid, peptide based, degradable particles, microemulsions, VPLs, attenuated bacterial or viral vectors) using any route of administration or ex vivo loading.

Vaccines are conventionally administered parenterally, by injection, for example, either subcutaneously or intramuscularly. Typically vaccines are prepared in an injectable form, either as a liquid solution or a suspension. Solid forms suitable for injection may also be prepared as emulsions, or with the immunogenic polypeptide, polypeptide fragment, or fusion protein encapsulated in liposomes. Additional formulations that are suitable for other modes of administration include suppositories and, in some cases, oral formulation or by nasal spray. For suppositories, traditional binders and carriers can include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like.

The vaccine composition takes the form of a solution, suspension, tablet, pill, capsule, sustained release formulation or powder, and contains an immunogenic effective amount of one or more of the disclosed CT491, CT601, CT687, CT732, CT781, CT808, CT823, CT062, CT104, and CT111 polypeptides, polypeptide fragments, fusion proteins, or DNA vaccines. In a typical composition, an immunogenic effective amount of the immunogenic polypeptide, polypeptide fragment, fusion protein, or DNA vaccine is about 1 µg to 10 mg per dose, and more desirably, about 5 µg to 5 mg per dose.

A vaccine is typically formulated for parenteral administration. Exemplary immunizations are carried out sub-cutaneously (SC), intramuscularly (IM), intravenously (IV), intraperitoneally (IP), or intra-dermally (ID).

The immunogenic CT491, CT601, CT687, CT732, CT781, CT808, CT823, CT062, CT104, or CT111 polypeptides, polypeptide fragments, or fusion proteins described herein can be formulated into the vaccine as neutral or salt forms. Pharmaceutically acceptable salts, include the acid addition salts (formed with the free amino groups of the polypeptide, polypeptide fragment, or fusion protein) and are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as are therapeutically effective and immunogenic. The quantity to be administered depends on the subject to be treated, capacity of the subject's immune system to host an immune response, and the degree of protection desired (e.g., prophylactic treatment or treatment of a patient with *Chlamydia*). The precise amount of CT491, CT601, CT687, CT732, CT781, CT808, CT823, CT062, CT104, and CT111 polypeptide, polypeptide fragment, fusion protein, or DNA vaccine required to be administered depends on the judgment of the practitioner and are peculiar to each subject. However, suitable dosage ranges are of the order of several hundred of micrograms active ingredient per subject. Suitable regimes for initial administration and booster shots are also variable, but are typified by an initial administration followed in intervals (weeks or months) by a subsequent injection or other administration.

Pharmaceutical Compositions

In addition to vaccines, the invention also provides pharmaceutical compositions that include one or more of the CT491, CT601, CT687, CT732, CT781, CT808, CT823, CT062, CT104, or CT111 polypeptides, polypeptide fragments, or fusion proteins of the present invention. The invention further provides pharmaceutical compositions that include one or more of the polypeptides, polypeptide fragments, or fusion proteins of the present invention in combination with one or more of the antigens disclosed in U.S. Patent Application Nos. 60/775,462; 60/817,471; and 60/963,215; herein incorporated by reference in their entirety. Such compositions may be incorporated into a pharmaceutically acceptable carrier, vehicle, or diluent.

In one embodiment, the pharmaceutical composition includes a pharmaceutically acceptable excipient. The compounds of the present invention may be administered by any suitable means, depending for example, on their intended use, as is well known in the art, based on the present description. For example, if the polypeptides, polypeptide fragments, or fusion proteins of the present invention are to be administered orally, they may be formulated as tablets, capsules, granules, powders, or syrups. Alternatively, formulations of the present invention may be administered parenterally as injections (intravenous, intramuscular, or subcutaneous), drop infusion preparations, or suppositories. For application by the ophthalmic mucous membrane route, the compounds of the present invention may be formulated as eye drops or eye ointments. Aqueous solutions are generally preferred for ocular administration, based on ease of formulation, biological compatibility, as well as a subject's ability to easily administer such compositions, for example, by means of instilling one to two drops of the solutions in the eye. However, the compositions may also be suspensions, viscous or semi-viscous gels, or other types of solid or semi-solid compositions.

The above-described formulations may be prepared by conventional means, and, if desired, the compounds may be mixed with any conventional additive, such as an excipient, a binder, a disintegrating agent, a lubricant, a corrigent, a solubilizing agent, a suspension aid, an emulsifying agent, or a coating agent.

Subject compounds may be suitable for oral, nasal, topical (including buccal and sublingual), rectal, vaginal, aerosol, and/or parenteral administration. The formulations may conveniently be presented in unit dosage form and may be prepared by any methods well known in the art of pharmacy. The amount of agent that may be combined with a carrier material to produce a single dose varies depending upon the subject being treated, and the particular mode of administration.

Pharmaceutical compositions of this invention suitable for parenteral administration includes one or more components of a supplement in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient, or suspending or thickening agents.

Methods of Treating Bacterial Infections

The polypeptide fragments, fusion proteins, pharmaceutical compositions, and vaccines described herein may be used in a variety of treatments of diseases including a bacterial infection, most preferably a *C. trachomatis* infection in a subject. Those skilled in the art will understand, the dosage of any composition described herein will vary depending, for example, on the symptoms, age, and body weight of the subject, the nature and severity of the infection to be treated or prevented, the route of administration, and the form of the supplement. Any of the subject formulations may be administered in any suitable dose, such as, for example, in a single dose or in divided doses. Dosages for the compounds of the present invention, alone or together with any other compound of the present invention, or in combination with any compound deemed useful for the particular infection to be treated, may be readily determined by techniques known to those skilled in the art. Also, the present invention provides mixtures of more than one subject compound, as well as other therapeutic agents.

The combined use of several compounds of the present invention, or alternatively other therapeutic agents, may reduce the required dosage for any individual component because the onset and duration of effect of the different components may be complimentary. In such combined therapy, the different active agents may be delivered together or separately, and simultaneously or at different times within the day.

Different bacterial infections that may be treated or prevented with the present invention include: *Chlamydia pneumoniae, Chlamydia psittaci*, and *Chlamydia trachomatis*.

Therapeutic Antibodies and T-cell Depletion

Alternatively, the immune response to *Chlamydia*, rather than the infection itself, may be responsible for symptoms that accompany infection, including sterility and pelvic inflammatory disease in a subject. In this case, it may be desirable to limit the immune response by a subset of $CD4^+$ or $CD8^+$ T cells within an infected subject. Antibodies which specifically recognize T cell clones targeted to the polypeptides, polypeptide fragments, or fusion proteins of the present invention, may therefore be useful in treating or preventing deleterious effects associated with *Chlamydia* infection. Methods for selective depletion of specific populations of T cells are described, for example, in Weinberg et al. (*Nature Med.* 2:183-189, 1966).

The following Example is meant to illustrate the invention and should not be construed as limiting.

Example 1

Determining whether a *C. trachomatis* Polypeptide, Polypeptide Fragment, or Fusion Protein is Immunogenic Methods A library of cells or viruses containing polynucleotides encoding *C. trachomatis* polypeptides, polypeptide fragments, or fusion proteins may be screened to determine which of the polypeptides, polypeptide fragments, or fusion proteins encoded by the polynucleotides are immunogenic. This may be accomplished by contacting each member of the library with a second cell (e.g., a macrophage or antigen presenting cell) capable of endocytosing the cell of the *C. trachomatis* library, and displaying portions of the expressed polypeptide of the library on the surface of the second cell (see, e.g., U.S. Pat. No. 6,008,415). The second cell is then contacted with a *C. trachomatis*-specific T cell (e.g., a *C. trachomatis*-specific CD4+ or CD8+ T cell) from an organism previously infected with *C. trachomatis*. The second cell may also be fixed (e.g., using paraformaldehyde) prior to contacting with a *C. trachomatis*-specific T cell. A *C. trachomatis*-specific T cell capable of binding a presented portion of the *C. trachomatis* protein, will result in secretion of cytokines. Cytokine secretion (e.g., secretion of IFN-γ, IL-2, or TNF) may be assayed for as known in the art, for example, using an ELISA assay.

In particular, murine $H2^b$ bone marrow-derived macrophages (BMMs) were seeded at a density of $1\times10^5$ cells/well in 96-well plates. Fourteen to sixteen hours later, an aliquot of a frozen *C. trachomatis* library was thawed. The media was aspirated from the BMMs and replaced with a library aliquot and 60 μl, of fresh RP-10 media. After 1 hour at 37° C., the BMMs were washed with PBS, 100 μL of RP-10 media added, and the cells incubated an additional hour at 37° C. The BMMs were then fixed with 1% paraformaldehyde for 15 minutes and washed extensively with PBS. BMM fixation was found to greatly reduce the background level of IFN-γ secretion by T cells. T cells (either *C. trachomatis*-specific CD4+ or CD8+ murine T cells; $1\times10^5$) were added to each well in 200 μL of RP-10 media. Plates were incubated for 18-24 hours at 37° C. and the amount of IFN-γ in the supernatant of each well determined through the use of an IFN-γ ELISA assay (Endogen).

Another way to identify an antigenic peptide is to pulse the polypeptide, polypeptide fragment, or fusion protein onto macrophages and screen for their ability to activate *C. trachomatis*-specific CD4+ or CD8+ murine T cells (as described above). Peptides used in such assays can be synthesized using methods known in the art. A polypeptide, polypeptide fragment, or fusion protein that is capable of activating the *C. trachomatis*-specific CD4+ or CD8+ murine T cells is deemed immunogenic.

*C. trachomatis*-Specific CD8+ Murine T Cells

An example of a protocol that may be used to produce *C. trachomatis*-specific $CD8^+$ murine T cells is provided below.

Pools of activated $CD8^+$ murine T cells for use in the identification of immunogenic *C. trachomatis* polypeptides, polypeptide fragments, and fusion proteins may be obtained using methods known in the art. Typically, in screening for antigens to pathogenic organisms, $CD8^+$ T cells are prepared from a mammal previously infected with the pathogenic organism. This preparation contains $CD8^+$ T cells specific for antigens from the pathogen.

*C. trachomatis*-specific $CD8^+$ T cells were harvested from mice as follows. A $C^{57}BL/6$ mouse was injected intraperitoneally with $10^7$ infection-forming units of *C. trachomatis*. Fourteen days later the mouse was euthanized and the spleen was harvested. The spleen was mashed through a 70 μm screen to create a single cell solution of splenocytes. The $CD8^+$ T cells were isolated from the splenocytes using anti-CD8 antibodies bound to MACS™ magnetic beads and separation protocols standard in the art (see, for e.g., MACS™ technology available from Miltenyi Biotec Inc., Auburn, Calif.). The isolated $CD8^+$ cells were added to macrophages of the same haplotype ($H2^b$), which were infected with *C. trachomatis* 18 hours prior in a 24-well dish. Irradiated splenocytes from a naïve mouse (C57BL/6) were added as feeder cells in media containing IL-2. The cells were incubated for 10 days during which the *C. trachomatis*-specific $CD8^+$ T cells were stimulated by the infected macrophages and replicated. On day 10, the $CD8^+$ T cells were stimulated again using macrophages infected with *C. trachomatis* (18 hours prior), and irradiated splenocytes. This procedure was repeated until sufficient amounts of $CD8^+$ T cells were present to screen the library.

$CD8^+$ T cells may also be cloned from a human subject as described by, for example, Hassell et al. (Immunology 79: 513-519, 1993).

*C. trachomatis*-Specific Murine $CD4^+$ T Cells

Activated $CD4^+$ murine T cells for use in the identification of immunogenic *C. trachomatis* polypeptides, polypeptide fragments, and fusion proteins may be obtained using methods known in the art. Splenocytes from mice were isolated 21 days after infection with *C. trachomatis* serovar L2 and cultured with irradiated (2,000 rad) bone marrow-derived dendritic cells, UV-inactivated *C. trachomatis* serovar L2, and naïve syngeneic splenocytes in RP-10 (RPMI medium 1640 supplemented with 10% fetal calf serum, L-glutamine, HEPES, 50 μM 2-β-mercaptoethanol, 50 units/ml penicillin, and 50 μg/ml streptomycin) with α-methyl mannoside and 5% supernatant from Con A-stimulated rat spleen cells. $CD8^+$ T cells were depleted from the culture by using Dynabeads Mouse CD8 (Invitrogen, Carlsbad, Calif.). The $CD4^+$ T cells were restimulated every 7 days with *C. trachomatis-pulsed* bone marrow-derived dendritic cells. Once a *C. trachomatis*-specific $CD4^+$ cell line was established, a $CD4^+$ T cell clone was isolated by limiting dilution.

$CD4^+$ T cells may also be cloned from a human subject as described by, for example, Hassell et al. (*Immunology* 79: 513-519, 1993).

This application is related to U.S. Application No. 60/775,462 filed Feb. 21, 2007; U.S. Application No. 60/817,471 filed Jun. 29, 2006; and U.S. Application No. 60/963,215 filed Aug. 3, 2007. The disclosures of U.S. Application Nos. 60/775,462; 60/817,471; and 60/963,215 are hereby incorporated by reference in their entirety.

All patents, patent applications, patent application publications, and other cited references are hereby incorporated by reference to the same extent as if each independent patent, patent application, or publication was specifically and individually indicated to be incorporated by reference.

What is claimed is:

1. A pharmaceutical composition comprising:
   (a) an isolated CT062 polypeptide comprising an amino acid sequence identical to SEQ ID NO: 8 or 9, wherein said polypeptide elicits at least a 40-fold increase in interferon-γ production from a population of T-lymphocytes compared to the level of interferon-γ production elicited from a non-antigenic peptide in the same assay; and
   (b) a pharmaceutically acceptable carrier.

2. The pharmaceutical composition of claim 1, wherein said polypeptide, when administered to a mammal, elicits an immune response.

3. The pharmaceutical composition of claim 1, wherein said polypeptide elicits a $CD8^+$ T-cell response.

4. The pharmaceutical composition of claim 1, wherein said amino acid sequence is SEQ ID NO: 8.

5. The pharmaceutical composition of claim 1, wherein said amino acid sequence is SEQ ID NO:9.

6. The pharmaceutical composition of claim 1 and an adjuvant.

7. The pharmaceutical composition of claim 1, wherein said adjuvant is selected from the group consisting of QS21, an aluminum salt, a calcium salt, an oil-in-water emulsion, a water-in-oil emulsion, a 7-substituted-8-oxo-guanosine derivative, a 8-sulfo-guanosine derivative, monophosphoryl lipid A, CPG, SBAS2, muramyl dipeptide, MF59, *Quillaja* saponins, and 3-De-O-acylated monophosphoryl lipid A.

8. The pharmaceutical composition of claim 1, wherein said polypeptide is a fusion protein that includes flagellin.

* * * * *